United States Patent
Okamoto et al.

(10) Patent No.: US 10,329,988 B2
(45) Date of Patent: Jun. 25, 2019

(54) APPARATUS FOR MEASURING AMMONIA CONCENTRATION, SYSTEM FOR MEASURING AMMONIA CONCENTRATION, SYSTEM FOR TREATING EXHAUST GAS, AND METHOD FOR MEASURING AMMONIA CONCENTRATION

(71) Applicant: NGK INSULATORS, LTD., Nagoya, Aichi (JP)

(72) Inventors: Taku Okamoto, Nagoya (JP); Yoshinobu Nakada, Nagoya (JP); Kosuke Monna, Nukata-gun (JP)

(73) Assignee: NGK Insulators, Ltd., Nagoya (JP)

(*) Notice: Subject to any disclaimer, the term of this patent is extended or adjusted under 35 U.S.C. 154(b) by 0 days.

(21) Appl. No.: 15/786,835

(22) Filed: Oct. 18, 2017

(65) Prior Publication Data
US 2018/0112582 A1   Apr. 26, 2018

Related U.S. Application Data

(60) Provisional application No. 62/411,736, filed on Oct. 24, 2016.

(30) Foreign Application Priority Data

Jun. 14, 2017   (JP) .................................. 2017-117089

(51) Int. Cl.
*F01N 3/20* (2006.01)
*F01N 11/00* (2006.01)
(Continued)

(52) U.S. Cl.
CPC .......... *F01N 11/007* (2013.01); *F01N 3/2066* (2013.01); *G01N 27/419* (2013.01);
(Continued)

(58) Field of Classification Search
USPC ................. 60/274, 276, 277, 285, 297, 301; 73/23.31, 23.32, 114.71, 114.72
See application file for complete search history.

(56) References Cited

U.S. PATENT DOCUMENTS

| 7,975,537 B2 * | 7/2011 | Wang | G01N 33/0054 73/114.71 |
| 8,359,841 B2 * | 1/2013 | Goya | F01N 3/208 60/295 |

(Continued)

FOREIGN PATENT DOCUMENTS

JP   5204160 B2   6/2013

OTHER PUBLICATIONS

Daniela Schonauer, et al.,"Selective mixed potential ammonia exhaust gas sensor", Sensor and Actuators B, vol. 140, (2009), p. 585-590.

*Primary Examiner* — Binh Q Tran
(74) *Attorney, Agent, or Firm* — Mattingly & Malur, PC

(57) ABSTRACT

An apparatus for measuring ammonia concentration measures ammonia concentration in a target gas with a sensor element including a mixed potential cell. The apparatus for measuring ammonia concentration includes an electromotive force acquisition section, an oxygen concentration acquisition section, and an ammonia concentration derivation section. The ammonia concentration derivation section derives the ammonia concentration in the target gas from the relationship represented by formula (1):

$$\text{EMF} = \alpha \log_a(p_{NH3}) - \beta \log_b(p_{O2}) + \gamma \log_c(p_{NH3}) \times \log_d(p_{O2}) + B \quad (1)$$

(where
EMF: an electromotive force of the mixed potential cell,
α, β, γ, and B: constants (provided that each of α, β, and γ≠0), (Continued)

a, b, c, and d: any base (provided that each of a, b, c, and d≠1, and each of a, b, c, and d>0),
$p_{NH_3}$: the ammonia concentration in the target gas, and
$p_{O_2}$: the oxygen concentration in the target gas).

9 Claims, 7 Drawing Sheets

(51) Int. Cl.
*G01N 33/00* (2006.01)
*G01N 27/416* (2006.01)
*G01N 27/419* (2006.01)

(52) U.S. Cl.
CPC ..... *G01N 27/4162* (2013.01); *G01N 33/0054* (2013.01); *F01N 2560/021* (2013.01); *F01N 2560/025* (2013.01); *F01N 2560/20* (2013.01); *F01N 2610/02* (2013.01); *Y02A 50/246* (2018.01); *Y02T 10/24* (2013.01)

(56) References Cited

U.S. PATENT DOCUMENTS

| | | |
|---|---|---|
| 8,382,973 B2 | 2/2013 | Sugaya et al. |
| 2006/0151338 A1* | 7/2006 | Wang ................. G01N 27/4071 205/780.5 |
| 2011/0048970 A1* | 3/2011 | Sugaya ............... G01N 27/419 205/781 |
| 2016/0356196 A1* | 12/2016 | Nakano ................. F01N 3/208 |

* cited by examiner

APPARATUS FOR MEASURING AMMONIA CONCENTRATION, SYSTEM FOR MEASURING AMMONIA CONCENTRATION, SYSTEM FOR TREATING EXHAUST GAS, AND METHOD FOR MEASURING AMMONIA CONCENTRATION

BACKGROUND OF THE INVENTION

1. Field of the Invention

The present invention relates to an apparatus for measuring ammonia concentration, a system for measuring ammonia concentration, a system for treating an exhaust gas, and a method for measuring ammonia concentration.

2. Description of the Related Art

Hitherto, ammonia sensors to detect ammonia concentrations in target gases such as exhaust gases of automobiles have been known. For example, Patent Literature 1 describes a multi-gas sensor including an ammonia sensing section having a pair of electrodes arranged on a solid electrolyte body. Formula (2) based on a mixed-potential formula is known as the characteristics of the electromotive force (EMF) of a mixed potential cell including solid electrolyte body and a pair of electrodes (for example, Non-Patent Literature 1).

[Math. 1]

$$EMF \propto \frac{RT}{2F}\left(\frac{2}{3}\ln p_{NH3} - \frac{1}{2}\ln p_{O2} - \ln p_{H2O}\right) \quad (2)$$

(where
EMF: the electromotive force of the mixed potential cell
R: a gas constant [J/(K·mol)]
T: the temperature of the mixed potential cell [K]
F: the Faraday constant [C/mol]
$p_{NH3}$: ammonia concentration in a target gas
$p_{O2}$: oxygen concentration in the target gas
$p_{H2O}$: H$_2$O concentration in the target gas)

CITATION LIST

Patent Literature

[PTL 1] Japanese Patent No. 5204160

Non Patent Literature

[NPL 1] D. Schonauer et al., Sensors and Actuators B vol. 140 (2009), p. 585-590

SUMMARY OF THE INVENTION

However, the inventors have conducted studies and have found that in actual sensor elements, the relationship among an electromotive force EMF, ammonia concentration $p_{NH3}$, oxygen concentration $p_{O2}$, H$_2$O concentration $p_{H2O}$ does not obey formula (2), in some cases. Thus, when the ammonia concentration $p_{NH3}$ is calculated from formula (2) in a mixed potential-type ammonia sensor, the ammonia concentration in the target gas is not accurately derived, in some cases.

The present invention has been accomplished in order to solve these problems and mainly aims to derive ammonia concentration in a target gas with higher accuracy.

In the present invention, the following measures are used in order to achieve the above-described main object.

An apparatus of the present invention for measuring ammonia concentration in a target gas with a sensor element including a mixed potential cell that includes a solid electrolyte body, a detection electrode arranged on the solid electrolyte body, and a reference electrode arranged on the solid electrolyte body, includes:

an electromotive force acquisition section configured to acquire information about an electromotive force of the mixed potential cell while the detection electrode is exposed to the target gas;

an oxygen concentration acquisition section configured to acquire information about oxygen concentration in the target gas; and an ammonia concentration derivation section configured to derive ammonia concentration in the target gas from the acquired information about the electromotive force, the acquired information about the oxygen concentration, and the relationship represented by formula (1):

$$EMF = \alpha \log_a(p_{NH3}) - \beta \log_b(p_{O2}) + \gamma \log_c(p_{NH3}) \times \log_d(p_{O2}) + B \quad (1)$$

(where
EMF: an electromotive force of the mixed potential cell,
α, β, γ, and B: constants (provided that each of α, β, and γ≠0),
a, b, c, and d: any base (provided that each of a, b, c, and d≠1, and each of a, b, c, and d>0),
$p_{NH3}$: the ammonia concentration in the target gas, and
$p_{O2}$: the oxygen concentration in the target gas).

In the apparatus for measuring ammonia concentration, the ammonia concentration in the target gas is derived from the information about the electromotive force of the mixed potential cell of the sensor element, the information about the oxygen concentration in the target gas, and the relationship of formula (1). In this way, the use of formula (1) can derive the ammonia concentration in the target gas with higher accuracy than that in the case of using formula (2) described above. Here, the derivation of the ammonia concentration on the basis of the relationship of formula (1) may be performed by using the relationship of formula (1) and is not limited to the derivation of the ammonia concentration using formula (1) itself. For example, the ammonia concentration may be derived from a formula obtained by modifying formula (1). The relationship among the values of the variables (EMF, $p_{NH3}$, $p_{O2}$) of formula (1) is stored in the form of a map, and the ammonia concentration may be derived from the map. The constants α, β, and B are values depending on the sensor element and can be determined by, for example, experiments in advance.

In this case, the target gas may have a temperature of 150° C. or higher. The target gas may have a 200° C. or higher. The target gas may have a temperature of 400° C. or lower.

A system of the present invention for measuring ammonia concentration includes the sensor element and the ammonia concentration measurement apparatus. Accordingly, the system for measuring ammonia concentration has the same effect as the apparatus of the present invention for measuring ammonia concentration, i.e., for example, the effect of deriving ammonia concentration in a target gas with higher accuracy.

In the system for measuring ammonia concentration, the detection electrode may be composed of a Au—Pt alloy as a main component. The Au—Pt alloy is suitable for a main component of the detection electrode because a mixed potential is easily established at the triple phase boundary of the solid electrolyte body and the target gas. In this case, the detection electrode may have a degree of concentration (=amount of Au present [atom %]/amount of Pt present [atom %]) of 0.3 or more, the degree of concentration being measured by at least one of X-ray photoelectron spectroscopy (XPS) and Auger electron spectroscopy (AES). A degree of concentration of 0.3 or more can more reliably establish the mixed potential. The degree of concentration may be 0.1 or more.

In the system of the present invention for measuring ammonia concentration, the sensor element may include a heater configured to heat the mixed potential cell to an operating temperature of 450° C. or higher and 650° C. or lower. In the system for measuring ammonia concentration, the use of an operating temperature of 450° C. or higher can appropriately activate the solid electrolyte body. In the system for measuring ammonia concentration, the use of an operating temperature of 650° C. or lower can inhibit a decrease in measurement accuracy due to the combustion of ammonia. The operating temperature may be 600° C. or lower.

A system of the present invention for treating an exhaust gas includes any one of the systems for measuring ammonia concentration according to the foregoing embodiments, and an exhaust gas path through which an exhaust gas serving as the target gas from an internal combustion engine flows, the sensor element being arranged in the exhaust gas path. Accordingly, the system for treating an exhaust gas has the same effect as the system for measuring ammonia concentration, i.e., for example, the effect of deriving ammonia concentration in a target gas with higher accuracy.

The system of the present invention for treating an exhaust gas may further include one or more oxidation catalysts arranged in the exhaust gas path, in which the sensor element may be arranged on the downstream side of the exhaust gas path in contrast to one of the one or more oxidation catalysts arranged at the upstream end. In this case, the target gas in which a component (for example, at least one of hydrocarbons and carbon monoxide) that is present in the target gas and that affects the measurement accuracy of the ammonia concentration has been oxidized by the oxidation catalysts reaches the sensor element. Thus, in the system for treating an exhaust gas, the ammonia concentration in the target gas can be derived with higher accuracy.

A method of the present invention for measuring ammonia concentration in a target gas with a sensor element including a mixed potential cell that includes a solid electrolyte body, a detection electrode arranged on the solid electrolyte body, and a reference electrode arranged on the solid electrolyte body, includes:

an electromotive force acquisition step of acquiring information about an electromotive force of the mixed potential cell while the detection electrode is exposed to the target gas;

an oxygen concentration acquisition step of acquiring information about oxygen concentration in the target gas; and a concentration derivation step of deriving the ammonia concentration in the target gas from the acquired information about the electromotive force, the acquired information about the oxygen concentration, and a relationship represented by formula (1):

$$EMF = \alpha \log_a(p_{NH3}) - \beta \log_b(p_{O2}) + \gamma \log_c(p_{NH3}) \times \log_d(p_{O2}) + B \quad (1)$$

(where
EMF: an electromotive force of the mixed potential cell,
$\alpha$, $\beta$, $\gamma$, and B: constants (provided that each of $\alpha$, $\beta$, and $\gamma \neq 0$),
a, b, c, and d: any base (provided that each of a, b, c, and d$\neq$1, and each of a, b, c, and d$>$0),
$p_{NH3}$: the ammonia concentration in the target gas, and
$p_{O2}$: the oxygen concentration in the target gas).

As with the foregoing apparatus for measuring ammonia concentration, the ammonia concentration in the target gas can be derived with higher accuracy from the relationship of formula (1) by the method for measuring ammonia concentration. In the method for measuring ammonia concentration, the apparatus for measuring ammonia concentration, the system for measuring ammonia concentration, and the system for treating an exhaust gas according to various embodiments may be used, and steps of providing these functions may be added.

DETAILED DESCRIPTION OF THE INVENTION

Figure 1:
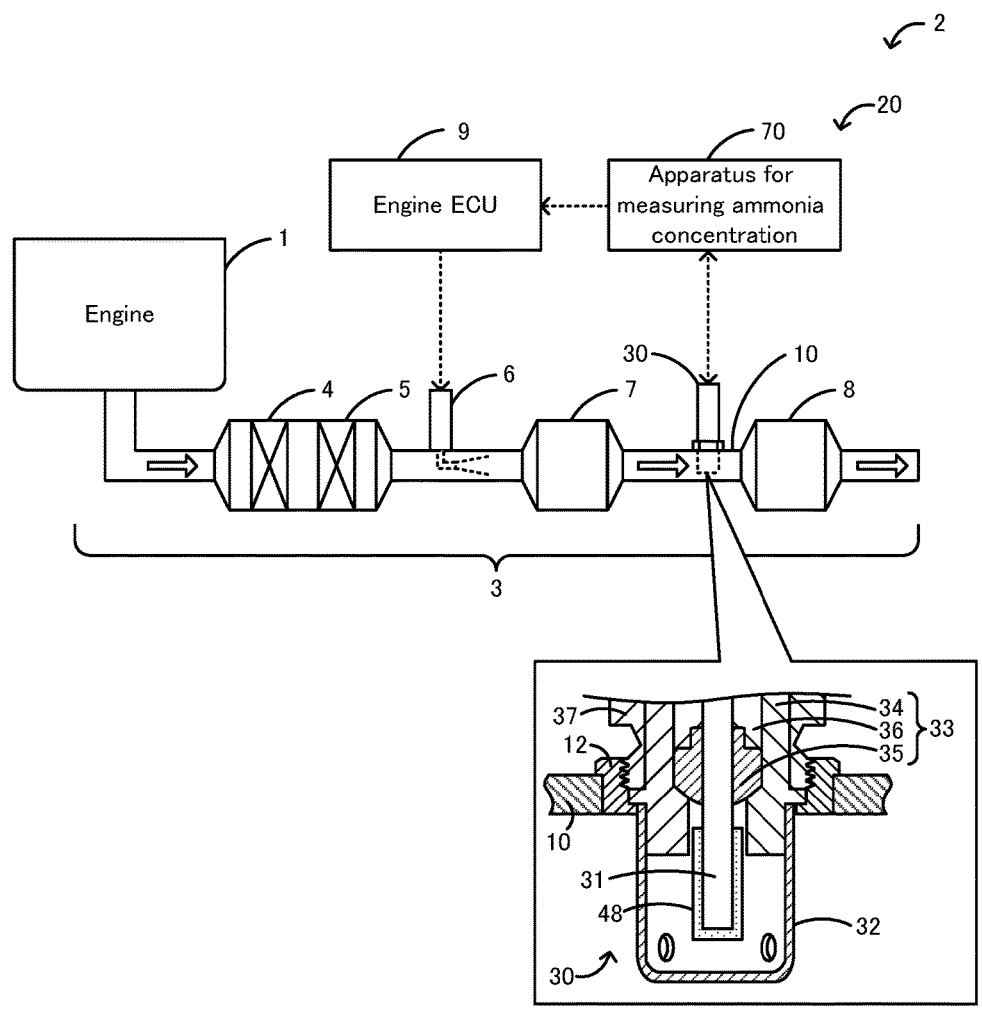
FIG. 1 is an explanatory drawing of a system 2 for treating an exhaust gas of an engine 1.
Figure 2:
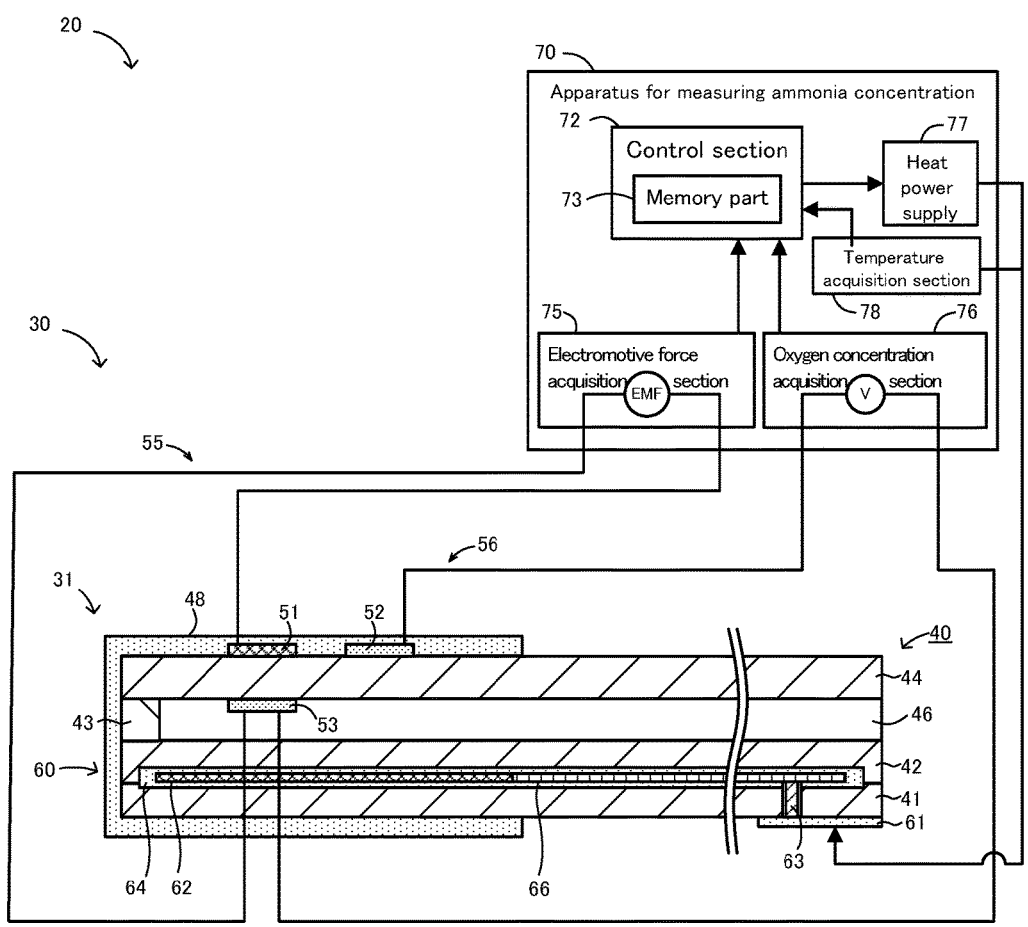
FIG. 2 is an explanatory drawing of a system 20 for measuring ammonia concentration.

Embodiments of the present invention will be described below with reference to the drawings. FIG. 1 is an explanatory drawing of a system 2 for treating an exhaust gas of an engine 1. FIG. 2 is an explanatory drawing of a system 20 for measuring ammonia concentration.

The system 2 for treating an exhaust gas is a system for treating an exhaust gas serving as a target gas from the engine 1. In this embodiment, the engine 1 is a diesel engine. As illustrated in FIG. 1, the system 2 for treating an exhaust gas includes an exhaust gas path 3 connected to the engine 1 and the system 20 for measuring ammonia concentration including a gas sensor 30 arranged in the exhaust gas path 3. In the system 2 for treating an exhaust gas, a diesel oxidation catalyst (DOC) 4, a diesel particulate filter (DPF) 5, an injector 6, a selective catalytic reduction (SCR) 7, the gas sensor 30, and an ammonia slip catalyst (ASC) 8 are arranged, in this order, from the upstream side toward the downstream side of the exhaust gas. The DOC 4 is one of oxidation catalysts included in the system 2 for treating an exhaust gas and converts HC and CO in the exhaust gas into water and carbon dioxide for detoxification. The DPF 5 traps PM in the exhaust gas. The injector 6 is a device configured to inject at least one of ammonia and a substance capable of forming ammonia (for example, urea) into an exhaust pipe to supply the at least one of ammonia and the substance to the SCR 7. In this embodiment, the injector 6 injects urea, and the injected urea is hydrolyzed to form ammonia. The SCR 7 decomposes nitrogen oxides (NOx) into harmless $N_2$ and $H_2O$ by reduction using ammonia supplied from the injector 6 into the exhaust pipe. The exhaust gas passing through the SCR 7 flows through a pipe 10. The gas sensor 30 is attached to the pipe 10. The ASC 8 is arranged downstream of the pipe 10. The ASC 8 is one of the oxidation catalysts included in the system 2 for treating an exhaust gas and is also referred to as a "downstream DOC" with respect to the DOC 4 (upstream DOC). That is, the system 2 for treating an exhaust gas according to this embodiment includes two oxidation catalysts: the DOC 4 and the ASC 8. The gas sensor 30 is arranged downstream in contrast to the DOC 4 arranged at the upstream end among one or more oxidation catalysts (two oxidation catalysts in this embodiment) included in the system 2 for treating an exhaust gas. The ASC 8 decomposes excessive ammonia in the exhaust gas passing through the SCR 7 into harmless $N_2$ and $H_2O$ by oxidation. The exhaust gas passing through the ASC 8 is released into, for example, air.

The system 20 for measuring ammonia concentration includes the gas sensor 30 and an apparatus 70 for measuring ammonia concentration, the apparatus being electrically connected to the gas sensor 30. The gas sensor 30 is an ammonia sensor configured to generate an electrical signal depending on the concentration of excessive ammonia contained in the target gas passing through the SCR 7 in the pipe 10. The gas sensor 30 also functions as an oxygen sensor configured to generate an electrical signal depending on the concentration of oxygen in the target gas and serves as a multi-sensor. The apparatus 70 for measuring ammonia concentration derives ammonia concentration in the target gas from the electrical signal generated by the gas sensor 30 and transmits the resulting data to an engine ECU 9. The engine ECU 9 controls the amount of urea injected from the injector 6 into the exhaust pipe in such a manner that the detected excessive ammonia concentration approaches zero. The system 20 for measuring ammonia concentration will be described in detail below.

As illustrated in FIG. 1, the gas sensor 30 is fixed in the pipe 10 in such a manner that the central axis of the gas sensor 30 is perpendicular to the flow of the target gas in the pipe 10. The gas sensor 30 may be fixed in the pipe 10 in such a manner that the central axis of the gas sensor 30 is perpendicular to the flow of the target gas in the pipe 10 and is tilted at a predetermined angle (for example, 45°) with respect to the vertical direction (an up and down direction of FIG. 1). As illustrated in the enlarged cross-sectional view of FIG. 1, the gas sensor 30 includes a sensor element 31, a protective cover 32 that covers and protects the front end side (the lower end side in FIG. 1) of the sensor element 31, which is an end side of the sensor element 31 in the longitudinal direction, an element fixing portion 33 that encapsulates and fix the sensor element 31, and a nut 37 fitted to the element fixing portion 33. The one end side of the sensor element 31 is covered with a porous protective layer 48.

The protective cover 32 is a cylindrical cover with a closed bottom, the cylindrical cover covering one end of the sensor element 31. Although a single-layer cover is used in FIG. 1, for example, two-or-more-layer cover including an inner protective cover and an outer protective cover may be used. The protective cover 32 has holes through which the target gas is allowed to flow into the protective cover 32. The one end of the sensor element 31 and the porous protective layer 48 are arranged in a cavity surrounded by the protective cover 32.

The element fixing portion 33 includes a cylindrical main metal fitting 34, a ceramic supporter 35 encapsulated in an inner through-hole of the main metal fitting 34, and a compact 36 that is encapsulated in the inner through-hole of the main metal fitting 34 and that is formed of a ceramic powder composed of, for example, talc. The sensor element 31 is located on the central axis of the element fixing portion 33 and extends through the element fixing portion 33 in the longitudinal direction. The compact 36 is compressed between the main metal fitting 34 and the sensor element 31. Thus, the compact 36 seals the through-hole in the main metal fitting 34 and fixes the sensor element 31.

The nut 37 is fixed coaxially with the main metal fitting 34 and has an external thread portion on an outer periphery thereof. The external thread portion of the nut 37 is fitted with a fitting member 12 that is welded to the pipe 10 and that has an internal thread portion on an inner periphery thereof. Thus, the gas sensor 30 can be fixed to the pipe 10 while the one end side of the sensor element 31 and the protective cover 32 protrude into the pipe 10.

The sensor element 31 will be described with reference to FIG. 2. The cross-sectional view of the sensor element 31 of FIG. 2 illustrates a sectional view taken along the central axis of the sensor element 31 in the longitudinal direction (cross section taken in the up and down direction of FIG. 1). The sensor element 31 includes a base 40 composed of an oxygen-ion-conducting solid electrolyte, a detection electrode 51 and an auxiliary electrode 52 arranged on the side of an end (the lower end of FIG. 1 and the left end of FIG. 2) of the sensor element 31 and on the upper surface of the base 40, a reference electrode 53 arranged inside the base 40, and a heater portion 60 that adjusts the temperature of the base 40.

The base 40 has a plate-like structure in which four layers, i.e., a first substrate layer 41, a second substrate layer 42, a spacer layer 43, and a solid electrolyte layer 44, are stacked, in this order, from the bottom in FIG. 2, each of the layers being formed of an oxygen-ion-conducting solid electrolyte layer composed of, for example, zirconia ($ZrO_2$). A solid electrolyte used to form these four layers is a dense, gas-tight material. The periphery of a portion of the base 40 in the protective cover 32 is exposed to the target gas introduced into the protective cover 32. A reference gas introduction cavity 46 is provided between an upper surface of the second substrate layer 42 and a lower surface of the solid electrolyte layer 44 in the base 40, a side portion of the cavity being defined by a side surface of the spacer layer 43. The reference gas introduction cavity 46 has an opening portion on the other end side (right end side of FIG. 2) remote from the one end side of the sensor element 31. For example, air is introduced into the reference gas introduction cavity 46, air serving as a reference gas used to measure ammonia concentration and oxygen concentration. Each of the layers of the base 40 may be formed of a substrate containing 3% to 15% by mole yttria ($Y_2O_3$) (yttria-stabilized zirconia (YSZ) substrate) serving as a stabilizer.

The detection electrode 51 is a porous electrode arranged on an upper surface of the solid electrolyte layer 44 of the base 40 in FIG. 2. The detection electrode 51, the solid electrolyte layer 44, and the reference electrode 53 form a mixed potential cell 55. In the mixed potential cell 55, a mixed potential (electromotive force EMF) is generated in the detection electrode 51, depending on the concentration of a predetermined gas component in the target gas. The value of the electromotive force EMF between the detection electrode 51 and the reference electrode 53 is used to derive the ammonia concentration in the target gas. The detection electrode 51 is composed of, as a main component, a material that establishes a mixed potential depending on the ammonia concentration and that has detection sensitivity to the ammonia concentration. The detection electrode 51 may be composed of a noble metal, such as gold (Au), as a main component. The detection electrode 51 is preferably composed of a Au—Pt alloy as a main component. The term "main component" used here refers to a component contained in a largest amount present (atm %, atomic percent) with respect to the total amount of components contained. The detection electrode 51 preferably has a degree of concentration (=amount of Au present [atom %]/amount of Pt present [atom %]) of 0.3 or more, the degree of concentration being measured by at least one of X-ray photoelectron spectroscopy (XPS) and Auger electron spectroscopy (AES). A degree of concentration of 0.3 or more can more reliably establish the mixed potential. The degree of concentration of the detection electrode 51 refers to the degree of surface concentration on a surface of noble metal particles of the detection electrode 51. The amount of Au present [atom %] is determined as the amount of Au present on the surfaces of the noble metal particles of the detection electrode 51. Similarly, the amount of Pt present [atom %] is determined as the amount of Pt present on the surfaces of the noble metal particles of the detection electrode 51. With regard to the surfaces of the noble metal particles, a surface (for example, an upper surface in FIG. 2) of the detection electrode 51 or a fracture surface of the detection electrode 51 may be used. For example, in the case where the surface (the upper surface in FIG. 2) of the detection electrode 51 is exposed, the degree of concentration can be measured on the surface; hence, the measurement may be performed by XPS. The degree of concentration may also be measured by AES. In the case where the detection electrode 51 is covered with the porous protective layer 48 as described in this embodiment, the fracture surface (fracture surface in the up and down direction of FIG. 2) of the detection electrode 51 is subjected to measurement by XPS or AES to determine the degree of concentration. A higher degree of concentration results in a smaller amount of Pt present on the surface of the detection electrode 51, thereby inhibiting the decomposition of ammonia in the target gas around the detection electrode 51 due to Pt. Thus, a higher degree of concentration results in a more improved derivation accuracy of the ammonia concentration in the system 20 for measuring ammonia concentration. Specifically, the degree of concentration is preferably 0.1 or more, more preferably 0.3 or more. The upper limit of the degree of concentration is not particularly set. For example, the detection electrode 51 may not contain Pt. The entire detection electrode 51 may be composed of Au. The detection electrode 51 has a porosity of, for example, 25% by volume to 60% by volume.

The auxiliary electrode 52 is a porous electrode arranged on the upper surface of the solid electrolyte layer 44, similarly to the detection electrode 51. The auxiliary electrode 52, the solid electrolyte layer 44, and the reference electrode 53 form an electrochemical concentration cell 56. In the concentration cell 56, an electromotive force difference V, which is a potential difference depending on the difference in oxygen concentration between the auxiliary electrode 52 and the reference electrode 53, is established. The value of the electromotive force difference V is used to derive the oxygen concentration (oxygen partial pressure) in the target gas. The auxiliary electrode 52 may be composed of a catalytically active noble metal. For example, Pt, Ir, Rh, Pd, or an alloy containing at least one thereof can be used for the auxiliary electrode 52. In this embodiment, the auxiliary electrode 52 is composed of Pt.

The reference electrode 53 is a porous electrode arranged on the lower surface of the solid electrolyte layer 44, i.e., arranged on a side of the solid electrolyte layer 44 opposite that on which the detection electrode 51 and the auxiliary electrode 52 are arranged. The reference electrode 53 is exposed in the reference gas introduction cavity 46, and a reference gas (here, air) in the reference gas introduction cavity 46 is introduced thereinto. The potential of the reference electrode 53 is the standard for the electromotive force EMF and the electromotive force difference V. The reference electrode 53 may be composed of a catalytically active noble metal. For example, Pt, Ir, Rh, Pd, or an alloy containing at least one thereof can be used for the reference electrode 53. In this embodiment, the reference electrode 53 is composed of Pt.

The porous protective layer 48 covers a surface of the sensor element 31 including the detection electrode 51 and the auxiliary electrode 52. For example, the porous protective layer 48 serves to inhibit the occurrence of cracking in the sensor element 31 due to the adhesion of water in the target gas. The porous protective layer 48 is composed of, for example, alumina, zirconia, spinel, cordierite, titania, or magnesia as a main component. In this embodiment, the porous protective layer 48 is composed of alumina. The thickness of the porous protective layer 48 is, but not particularly limited to, for example, 20 to 1,000 μm. The porosity of the porous protective layer 48 is, but not particularly limited to, for example, 5% by volume to 60% by volume. The sensor element 31 may not include the porous protective layer 48.

The heater portion 60 serves to control the temperature of the base 40 (in particular, the solid electrolyte layer 44) by heating and keeping it warm in order to activate the solid electrolyte of the base 40 to increase the oxygen-ion conductivity. The heater portion 60 includes a heater electrode 61, a heater 62, a through-hole 63, a heater insulating layer 64, and a lead wire 66. The heater electrode 61 is an electrode arranged so as to be in contact with a lower surface of the first substrate layer 41. The heater electrode 61 is connected to a heater power supply 77 of the apparatus 70 for measuring ammonia concentration.

The heater 62 is an electrical resistor arranged so as to be held between the first substrate layer 41 and the second substrate layer 42. The heater 62 is connected to the heater electrode 61 through the lead wire 66 and the through-hole 63. The heater 62 is fed from the heater power supply 77 through the heater electrode 61 to generate heat, so that the base 40 included in the sensor element 31 is heated and kept warm. The heater 62 is configured to be able to control the output with a temperature sensor (here, temperature acquisition section 78) in such a manner that the mixed potential cell 55 and the concentration cell 56 (in particular, the solid electrolyte layer 44) have a predetermined operating temperature. The operating temperature is preferably 450° C. or higher because the solid electrolyte layer 44 of the mixed potential cell 55 can be appropriately activated. The operating temperature is preferably 650° C. or lower because it is possible to inhibit a decrease in the measurement accuracy due to the combustion of ammonia. The operating temperature may be 600° C. or lower. The heater insulating layer 64 is an insulating layer that is arranged on upper and lower surfaces of the heater 62 and that is composed of an insulating material such as alumina, specifically porous alumina.

The apparatus 70 for measuring ammonia concentration is an apparatus for measuring the ammonia concentration in the target gas with the sensor element 31. The apparatus 70 for measuring ammonia concentration also serves as a controller of the sensor element 31. The apparatus 70 for measuring ammonia concentration includes a control section 72, an electromotive force acquisition section 75, an oxygen concentration acquisition section 76, the heater power supply 77, and the temperature acquisition section 78.

The control section 72 controls the entire apparatus and, for example, is a microprocessor including CPU, RAM, and so forth. The control section 72 includes a memory part 73 that stores a processing program and various data sets. The electromotive force acquisition section 75 is a module that acquires information about the electromotive force EMF of the mixed potential cell 55. In this embodiment, the electromotive force acquisition section 75 is connected to the detection electrode 51 and the reference electrode 53 of the mixed potential cell 55 and thus functions as a voltage detection circuit that measures an electromotive force EMF. The oxygen concentration acquisition section 76 is a module that acquires information about the oxygen concentration in the target gas. In this embodiment, the oxygen concentration acquisition section 76 is connected to the auxiliary electrode 52 and the reference electrode 53 of the concentration cell 56 and thus functions as a voltage detection circuit that measures the electromotive force difference V serving as information about the oxygen concentration. The electromotive force acquisition section 75 and the oxygen concentration acquisition section 76 output the electromotive force EMF and the electromotive force difference V that have been measured by them to the control section 72. The control section 72 derives the ammonia concentration in the target gas from the electromotive force EMF and the electromotive force difference V. The heater power supply 77 is a power supply that supplies power to the heater 62, and the output power is controlled by the control section 72. The temperature acquisition section 78 is a module that acquires a value about the temperature of the heater 62 (here, value of resistance). The temperature acquisition section 78 acquires the value of resistance of the heater 62 by, for example, connecting the temperature acquisition section 78 to the heater electrode 61, allowing a minute electric current to flow, and measuring a voltage.

Each of the detection electrode 51, the auxiliary electrode 52, and the reference electrode 53 is electrically connected to a corresponding one of lead wires arranged toward the other end of the sensor element 31 (right side of FIG. 2) (not illustrated in FIG. 2). The electromotive force acquisition section 75 and the oxygen concentration acquisition section 76 measure the electromotive force EMF and the electromotive force difference V, respectively, through the lead wires.

Figure 3:
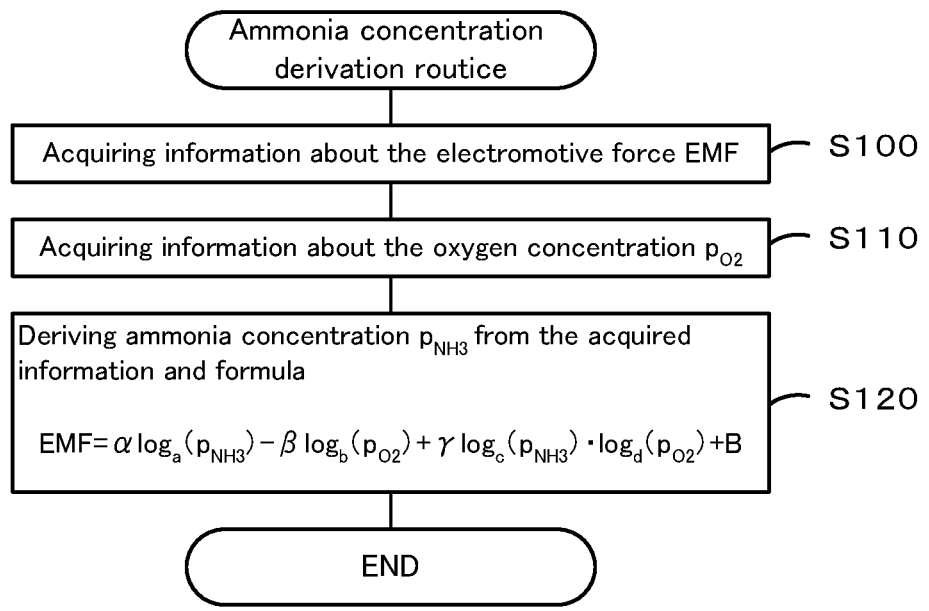
FIG. 3 is a flow chart illustrating an example of an ammonia concentration derivation routine.

The measurement of the ammonia concentration with the system 20 for measuring ammonia concentration will be described below. FIG. 3 is a flow chart illustrating an example of an ammonia concentration derivation routine executed by the control section 72. The routine is stored in, for example, the memory part 73 of the control section 72. When a command to derive ammonia concentration is fed from the engine ECU 9, the routine is repeatedly executed, for example, with a predetermined period (for example, several milliseconds to several tens of milliseconds). The control section 72 controls, in advance, the temperature of the mixed potential cell 55 and the concentration cell 56 to a predetermined operating temperature (for example, a temperature in the range of 450° C. or higher and 650° C. or lower) by controlling the output power of the heater power supply 77 to produce heat from the heater 62. For example, the control section 72 controls the temperature of the mixed potential cell 55 and the concentration cell 56 to a predetermined operating temperature by controlling the output power of the heater power supply 77 in such a manner that the temperature (here, resistance) of the heater 62 acquired by the temperature acquisition section 78 is a predetermined value.

When the ammonia concentration derivation routine is started, the control section 72 executes an electromotive force acquisition step of acquiring information about the electromotive force EMF of the mixed potential cell 55 with the electromotive force acquisition section 75 (step S100). In this embodiment, the control section 72 acquires the value of the electromotive force EMF measured by the electromotive force acquisition section 75 on an as-is basis. The control section 72 executes the ammonia concentration derivation routine in a state in which, basically, an exhaust gas from the engine 1 flows through the pipe 10 and the protective cover 32. Thus, the control section 72 acquires the electromotive force EMF of the mixed potential cell 55 while the detection electrode 51 is exposed to the target gas. Here, in the mixed potential cell 55, electrochemical reactions, such as the oxidation of ammonia and the ionization of oxygen in the target gas, occur at the triple phase boundary of the detection electrode 51, the solid electrolyte layer 44 and the target gas to establish a mixed potential on the detection electrode 51. Thus, the electromotive force EMF is a value based on the ammonia concentration and the oxygen concentration in the target gas.

The control section 72 executes an oxygen concentration acquisition step of acquiring information about oxygen concentration in the target gas with the oxygen concentration acquisition section 76 (step S110). In this embodiment, the control section 72 acquires the electromotive force difference V of the concentration cell 56 from the oxygen concentration acquisition section 76. Here, in the concentration cell 56, the electromotive force difference V is generated between the auxiliary electrode 52 and the reference electrode 53, depending on the difference in oxygen concentration between the target gas and air in the reference gas introduction cavity 46. Hydrocarbons, $NH_3$, CO, NO, $NO_2$ in the target gas are subjected to redox by the catalysis of Pt serving as the auxiliary electrode 52. The concentrations of these gas components in the target gas are significantly lower than the oxygen concentration in the target gas. Thus, the occurrence of the redox has little influence on the oxygen concentration in the target gas. Accordingly, the electromotive force difference V is a value based on the oxygen concentration in the target gas. By the control section 72, any one of step S100 and step S110 may be first executed, or the steps may be executed in parallel.

Subsequently, the control section 72 executes a concentration derivation step of deriving ammonia concentration in the target gas from the information about the electromotive force EMF acquired in step S100, the information about the oxygen concentration acquired in step S110, and the relationship represented by formula (1) (step S120) and terminates the routine. The relationship represented by formula (1) is stored in, for example, the memory part 73, in advance.

$$EMF = \alpha \log_a(p_{NH3}) - \beta \log_b(p_{O2}) + \gamma \log_c(p_{NH3}) \times \gamma \log_c(p_{NH3}) \times \log_d(p_{O2}) + B \quad (1)$$

(where
EMF: an electromotive force of the mixed potential cell,
$\alpha$, $\beta$, $\gamma$, and B: constants (provided that each of $\alpha$, $\beta$, and $\gamma \neq 0$),
a, b, c, and d: any base (provided that each of a, b, c, and d $\neq$ 1, and each of a, b, c, and d > 0),
$p_{NH3}$: the ammonia concentration in the target gas, and
$p_{O2}$: the oxygen concentration in the target gas).

In step S120, the control section 72 replaces "EMF" in formula (1) by the value of the electromotive force EMF acquired in step S100. The control section 72 derives the oxygen concentration $p_{O2}$ from the electromotive force difference V acquired in step S110 and the relationship, which is stored in the memory part 73 in advance, between the electromotive force difference V and the oxygen concentration $p_{O2}$ and replaces "$p_{O2}$" in formula (1) by the derived value. The control section 72 derives the ammonia concentration $p_{NH3}$ in formula (1). The units of the electromotive force EMF may be, for example, [mV]. The ammonia concentration $p_{NH3}$ is the volume fraction of ammonia in the target gas. The oxygen concentration $p_{O2}$ is the volume fraction of oxygen in the target gas. With regard to the units of $p_{NH3}$ and $p_{O2}$, a value given in parts per million [ppm] may be used, a value given in percent [%] may be used, or a dimensionless value (for example, in the case of 10%, the value is 0.1) may be used. $p_{NH3}$ and $p_{O2}$ may be given in different units. Each of the bases a, b, c, and d may be a value of 10 or Napier's constant e. Each of the constants $\alpha$, $\beta$, $\gamma$, and B has a value determined, depending on the sensor element 31 and can have different values, depending on the sensor element 31. The constants $\alpha$, $\beta$, $\gamma$, and B can be determined by, for example, experiments described below, in advance. The constants $\alpha$ and $\beta$ may satisfy $\alpha:\beta \neq (\frac{2}{3}):(\frac{1}{2})$. The constants $\alpha$ and $\beta$ may have a positive value. The constant $\gamma$ may have a positive value or a negative value. The derivation of the ammonia concentration $p_{NH3}$ executed by the control section 72 on the basis of the relationship of formula (1) may be performed using the relationship of formula (1) and is not limited to the derivation of the ammonia concentration using formula (1) itself. For example, formula (1) itself may be stored in the memory part 73. Formula (1a) or (1b), described below, obtained by modifying the formula (1) may be stored. Formula (1c), described below, obtained by modifying the formula (1a) in such a manner that the left side is "$p_{NH3}$" alone may be stored. The relationship of values of the variables (EMF, $p_{NH3}$, and $p_{O2}$) of formula (1) is stored as a map in the memory part 73. The control section 72 may derive the ammonia concentration $p_{NH3}$ from the map.

$$EMF = (\alpha + \gamma' \log_d(p_{O2})) \log_a(p_{NH3}) - \beta \log_b(p_{O2}) + B \quad (1a)$$

(where $\gamma' = \gamma/\log_a c$)

$$EMF = \alpha \log_a(p_{NH3}) - (\beta - \gamma'' \log_c(p_{NH3})) \log_b(p_{O2}) + B \quad (1b)$$

(where $\gamma'' = \gamma/\log_b d$)

[Math. 2]

$$p_{NH3} = a^{(EMF + \beta \log_b(p_{O2}) - B)/(\alpha + \gamma' \log_d(p_{O2}))} \quad (1c)$$

$$\left(\text{where } \gamma' = \frac{\gamma}{\log_a c}\right)$$

As described above, the control section 72 derives the ammonia concentration $p_{NH3}$ in the target gas from the relationship of formula (1) in this embodiment. Thus, the ammonia concentration in the target gas can be derived with high accuracy, compared with, for example, in the case of using formula (2) described above. This will be described below.

As described above, formula (2) is known as the characteristics of the electromotive force EMF of the mixed potential-type ammonia sensor. However, the inventors have conducted studies and have found that in an actual sensor element (for example, the sensor element 31), the relationship among the electromotive force EMF, the ammonia concentration $p_{NH3}$, the oxygen concentration $p_{O2}$, the $H_2O$ concentration $p_{H2O}$ does not obey formula (2). For example, although the relationship between the degree of the effect of the ammonia concentration $p_{NH3}$ on the electromotive force EMF ($NH_3$ sensitivity) and the degree of the effect of the oxygen concentration $p_{O2}$ on the electromotive force EMF ($O_2$ interference) should be $NH_3$ sensitivity:$O_2$ interference= $(\frac{2}{3}):(\frac{1}{2})$ from the coefficients of the term $p_{NH3}$ and the term $p_{O2}$ in the right side of formula (2), the relationship was not obtained, in some cases. According to formula (2), although the effect of the $H_2O$ concentration $p_{H2O}$ on the electromotive force EMF ($H_2O$ interference) should be present, in fact, even when the $H_2O$ concentration $p_{H2O}$ in the target gas was changed, the electromotive force EMF remained substantially unchanged.

With regard to the oxidation of ammonia and the ionization of oxygen in the target gas, an anodic reaction represented by equation (a) described below and a cathodic reaction represented by equation (b) described below occur at the triple phase boundary of the mixed potential cell 55. Equations (a) and (b) can also be expressed as equations (a)' and (b)'. In equation (a), "$O_O$" represents an oxygen ion ($O^{2-}$) present in an oxygen site in the solid electrolyte layer 44. The fourth term in the right side of equation (a) indicates that an oxygen ion is not present (not sufficient) in the oxygen site in the solid electrolyte layer 44.

[Math. 3]

[Anodic reaction]

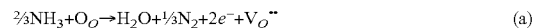

$$\frac{2}{3}NH_3 + O_O \rightarrow H_2O + \frac{1}{3}N_2 + 2e^- + V_O^{\cdot\cdot} \quad (a)$$

$$NH_3 + O_2 \rightarrow H_2O + N_2 + e^- \quad (a)'$$

[Cathodic reaction]

$$\frac{1}{2}O_2 + 2e^- + V_O^{\cdot\cdot} \rightarrow O_O \quad (b)$$

$$O_2 + 4e^- \rightarrow 2O^{2-} \quad (b)'$$

The anodic reaction and the cathodic reaction occur simultaneously at the triple phase boundary of one detection electrode (for example, the detection electrode 51) to form a local cell, thereby establishing an electromotive force EMF. This is a mixed potential cell (for example, the mixed potential cell 55). The electromotive force EMF at this time should theoretically obey formula (2). For example, the coefficient "$\frac{2}{3}$" of the ammonia concentration $p_{NH3}$ in formula (2) is a value based on the coefficient "$\frac{2}{3}$" of $NH_3$ on the left side of equation (a). Similarly, the coefficient "½" of the oxygen concentration $p_{O2}$ in the formula (2) and the coefficient "1" of the $H_2O$ concentration $pH_2O$ are values based on the coefficient "½" of $O_2$ on the left side of equation (b) and the coefficient "1" of $H_2O$ on the right side of equation (a), respectively.

For actual sensor elements, however, it was found in experiments that the relationship among the variables obeys formula (1), and not formula (2). The inventors have considered that the reason for this that $p_{NH3}$, $p_{O2}$, and $p_{H2O}$ in formula (2) need not be replaced by the concentrations in the target gas and should be replaced by partial pressures at the triple phase boundary. Letting an $NH_3$ partial pressure, an $O_2$ partial pressure, and a $H_2O$ partial pressure at the triple phase boundary on the detection electrode be $p_{NH3}^*$, $p_{O2}^*$, and $p_{H2O}^*$, respectively, formula (A1) holds. This can also be derived from formula (2). The actual electromotive force EMF seemingly obeys formula (A1), and not formula (2). Because $p_{NH3}^*$, $p_{O2}^*$, and $p_{H2O}^*$ at the triple phase boundary cannot be directly detected, a formula including $p_{NH3}$, $p_{O2}$, and $p_{H2O}$ in the target gas need to be derived from formula (A1). The inventors thought that we could explain below that formula (1) including $p_{NH3}$, $p_{O2}$, and $p_{H2O}$ holds on the basis of formula (A1).

[Math. 4]

$$EMF \propto \frac{RT}{2F}\left(\frac{2}{3}\ln p_{NH3}^* - \frac{1}{2}\ln p_{O2}^* - \ln p_{H2O}^*\right) \quad (A1)$$

Let us first consider a mixed potential equation from a microscopic point of view. As described above, the partial pressures, $\ln p_{NH3}^*$, $\ln p_{O2}^*$, and $\ln p_{H2O}^*$, at the triple phase boundary on the detection electrode are not equal to the partial pressures, $\ln p_{NH3}$, $\ln p_{O2}$, and $\ln p_{H2O}$, in an atmospheric gas (target gas). This is because the following dynamic changes occur in the electrochemical reactions: molecules are adsorbed onto a surface of the detection electrode, diffused on the surface of the detection electrode to reach the triple phase boundary, and subjected to electrochemical reactions, and the resulting products are desorbed from the surface of the detection electrode, rather than the fact that the molecules directly reach the triple phase boundary from the gas phase. Let us now consider the product $H_2O$ formed in the anodic reaction. The formed $H_2O$ is seemingly adsorbed on the detection electrode and then desorbed into the gas phase. Because a large amount of $H_2O$ is present in the target gas, the $H_2O$ formed in the anodic reaction seems to be not readily desorbed from the surface of the detection electrode. It is thus considered that the $H_2O$ partial pressure $p_{H2O}^*$ at the triple phase boundary during the adsorption of $H_2O$ is larger than the $H_2O$ partial pressure $p_{H2O}$ in the target gas and that formula (A2) described below always holds. In the target gas (here, an exhaust gas), the $H_2O$ concentration is usually about 5% to about 15%, and the total pressure remains constant at 1 atm. For the sake of safety, considering that the $H_2O$ concentration changes in a wide range of 1% to 20%, formula (A3) described below holds.

$$p_{H2O}^* > p_{H2O} \quad (A2)$$

$$0.01 \text{ atm} \leq p_{H2O} < 0.2 \text{ atm} \quad (A3)$$

Let us next consider that what will become of $p_{H2O}^*$ when $p_{H2O}$ is changed while $H_2O$ is adsorbed on the surface of the detection electrode. With regard to $H_2O$ at the triple phase boundary, $H_2O$ adsorbed on the detection electrode is denoted by $H_2O(ad)$, and $H_2O$ in the gas phase is denoted by $H_2O(gas)$. The partial pressure of $H_2O$ adsorbed on the detection electrode is denoted by $p_{H2O(ad)}$, and the partial pressure of $H_2O$ in the gas phase is denoted by $p_{H2O(gas)}$. Thus, $p_{H2O}^* = p_{H2O(ad)} + p_{H2O(gas)}$. $p_{H2O(ad)}$ includes the partial pressure of $H_2O$ that comes from the target gas and that is adsorbed on the detection electrode, and the partial pressure of $H_2O$ that is formed by the anodic reaction (the foregoing equations (a) and (a)') and that is adsorbed on the detection electrode. $p_{H2O(gas)}$ includes the partial pressure of $H_2O$ that is contained in the target gas and that is present at the triple phase boundary in a gas phase state, and the partial pressure of $H_2O$ that is formed by the anodic reaction and that is in a gas phase state. With regard to $H_2O(ad)$ and $H_2O(gas)$, formulae (A4) and (A5) described below hold, provided that an equilibrium constant K=(constant). Although $p_{H2O}^*$ is supposed to be changed according to formulae (A4) and (A5), in fact, it behaves differently. The reason for this is presumably that $p_{H2O}$ changes in the range represented by formula (A3) described above, whereas $p_{H2O(ad)}$ cannot change once the adsorption of $H_2O$ on the detection electrode is stabilized and reaches a steady state (=1 atm). The reason $p_{H2O(ad)}$ is 1 atm in the steady state is described below. Because $H_2O_{(ad)}$ adsorbed on the detection electrode is not in the gas phase, the amount of $H_2O(ad)$ is expressed as activity $a_{H2O(ad)}$, and not as partial pressure, to be exact. When $H_2O(ad)$ is regarded as a solid, the activity $a_{H2O(ad)}$ have a value of 1 (i.e., the activity is 1 irrespective of the amount adsorbed on the detection electrode), and an activity of 1 can be regarded as comparable to a partial pressure of 1 atm.

[Math. 5]

$$H_2O(ad) \overset{K}{\rightleftharpoons} H_2O(gas) \quad (A4)$$

$$K = \frac{p_{H2O(ad)}}{p_{H2O(gas)}} = \frac{p_{H2O}^* - p_{H2O(gas)}}{p_{H2O(gas)}} \quad (A5)$$

Accordingly, $p_{H2O(ad)}$ can be regarded as 1 atm. Although as with formula (A3), $p_{H2O(gas)}$ seems to be about 0.01 to about 0.2 atm, because $H_2O(ad)$, which can be regarded as 1 atm, is present on the surface of the detection electrode, $H_2O$ in the gas phase is less likely to contribute to the reaction, the partial pressure $p_{H2O(gas)}$ of $H_2O$ present in the gas phase at the triple phase boundary seems to have a value significantly smaller than 0.01 to 0.2 atm. Thus, $p_{H2O(ad)} \gg p_{H2O(gas)}$ seemingly holds, and $p_{H2O(gas)}$ seems to have a very small, negligible value. Accordingly, even if $p_{H2O}$ changes while $H_2O$ is adsorbed on the surface of the detection electrode, $p_{H2O}^*$ can be regarded as constant, as represented by formula (A6). Thus, formula (A1) can be regarded as formula (A7). That is, the $H_2O$ partial pressure $p_{H2O}^*$ at the triple phase boundary can be regarded as having no effect ($H_2O$ interference) on the electromotive force EMF.

[Math. 6]

$$p_{H2O}^* = p_{H2O(ad)} + p_{H2O(gas)} \dot{=} p_{H2O(ad)} = \text{constant } (1 \text{ atm}) \quad (A6)$$

$$EMF \propto \frac{RT}{2F}\left(\frac{2}{3}\ln p^*_{NH3} - \frac{1}{2}\ln p^*_{O2}\right) \quad (A7)$$

Let us then consider a mixed potential equation from a macroscopic point of view. When the total pressure of the target gas is 1 atm, the concentration is equal to the partial pressure; thus, $p_{NH3}$, $p_{O2}$, and $p_{H2O}$ will be explained below as partial pressures. Formula (A8) can be derived from formula (A3). Formula (A9) can be derived from formula (A6). From formulae (A8) and (A9), formula (A10) holds. Letting the ratio of ln $p_{H2O}{}^*$ to ln $p_{H2O}$ be a pressure adjustment factor δ, δ is defined by formula (A11). From formula (A10), δ satisfies −1<δ<1. Similarly, letting the ratio of ln $p_{NH3}{}^*$ to ln $p_{NH3}$ be a pressure adjustment factor δ', δ' is defined by formula (A12). The pressure adjustment factors δ and δ' are values characteristic of the sensor element, depending on, for example, the composition and the structure of the detection electrode.

$$-4.6 < \ln p_{H2O} < -1.6 \quad (A8)$$

$$\ln p_{H2O}{}^* \approx 0 \quad (A9)$$

$$|\ln p_{H2O}{}^*| < |\ln p_{H2O}| \quad (A10)$$

$$\delta = \ln p_{H2O}{}^*/\ln p_{H2O} \quad (A11)$$

$$\delta' = \ln p_{NH3}{}^*/\ln p_{NH3} \quad (A12)$$

Formula (A1) is transformed using the pressure adjustment factors δ and δ' to derive formula (A13). Formula (A13) is obtained by substituting ln $p_{H2O}{}^* = \delta \times \ln p_{H2O}$ obtained from formula (A11), ln $p_{NH3}{}^* = \delta \times \ln p_{NH3}$ obtained from formula (A12), and ln $p_{O2}{}^* = \ln p_{O2}$ in formula (A1). In existing O₂ sensors and SOFCs, it is well known that the relationship between the oxygen concentration and the electromotive force obeys the Nernst equation; hence, it is clear that ln $p_{O2}{}^* = \ln p_{O2}$ holds.

[Math. 7]

$$EMF \propto \frac{RT}{2F}\left(\frac{2}{3}\delta'\ln p_{NH3} - \frac{1}{2}\ln p_{O2} - \delta\ln p_{H2O}\right) \quad (A13)$$

From formulae (A6) and (A11), ln $p_{H2O}{}^* = \delta \times \ln p_{H2O} = 0$ holds. Thus, formula (A13) can be expressed as formula (A14). Formula (A14) can be expressed as formula (A15). The constants A and B are values characteristic of the sensor element, depending on, for example, the composition and the structure of the detection electrode. In formula (A15), letting the base of the logarithm be freely selected values a and b and letting the coefficients of the terms in the right side be constants α and β, formula (A16) described below is derived.

[Math. 8]

$$EMF \propto \frac{RT}{2F}\left(\frac{2}{3}\delta'\ln p_{NH3} - \frac{1}{2}\ln p_{O2}\right) \quad (A14)$$

$$EMF \propto A\frac{RT}{2F}\left(\frac{2}{3}\delta'\ln p_{NH3} - \frac{1}{2}\ln p_{O2}\right) + B \quad (A15)$$

(where A and B are constants)

$$EMF = \alpha\log_a(p_{NH3}) - \beta\log_b(p_{O2}) + B \quad (A16)$$

Unlike formula (2), formula (A16) can express the fact that the relationship, $p_{NH3}$ sensitivity:$p_{O2}$ sensitivity=(⅔): (½), does not always hold and that substantially no H₂O interference is present. Thus, the use of formula (A16) can derive the ammonia concentration $p_{NH3}$ with high accuracy, compared with formula (2).

The inventors have conducted further studies and have found the following: According to formula (A16), the relationship between the ammonia concentration $p_{NH3}$ and the electromotive force EMF will be a linear one with a slope of the constant α, and the constant α will not vary as the oxygen concentration $p_{O2}$ is changed; however, in fact, the constant α varies depending on the oxygen concentration $p_{O2}$. For example, a higher oxygen concentration $p_{O2}$ had a tendency to lead to a steeper slope of a straight line expressing the relationship between the ammonia concentration $p_{NH3}$ and the electromotive force EMF, in some cases. Furthermore, it was also found that the relationship between the logarithm of the oxygen concentration $p_{O2}$ and the slope of the straight line expressing the relationship between the ammonia concentration $p_{NH3}$ and the electromotive force EMF is one expressed by a straight line (linear function). Thus, the relationship was reflected in formula (A16) to derive formula (1a), and formula (1a) was transformed to derive formula (1). Formula (1) corresponds to a formula obtained by the addition of the term "γ $\log_c(p_{NH3}) \times \log_d(p_{O2})$" to formula (A16). This term is affected by both of the ammonia concentration $p_{NH3}$ and the oxygen concentration $p_{O2}$ and is thus referred to as an "interaction term". The use of formula (1) can derive the ammonia concentration $p_{NH3}$ with higher accuracy than that in the case of using formula (A16).

An exact reason the interaction term affects the electromotive force EMF is not clear. However, the interaction term seemingly expresses the occurrence of the gas-phase combustion of ammonia and oxygen before the target gas reaches the triple phase boundary. For example, it is believed that because each of the porous protective layer 48 and the detection electrode 51 is a porous material, when the target gas passes through pores of at least one of them, ammonia molecules collide with oxygen molecules to burn. A larger amount of ammonia burned reduces larger amounts of ammonia and oxygen before ammonia and oxygen in the target gas reach the triple phase boundary; thus, ammonia and oxygen in the target gas seemingly have less effect on the electromotive force EMF. The interaction term seems to express an increase or a decrease in electromotive force EMF depending on the amount burned.

The constant γ in the interaction term is a value characteristic of the sensor element, depending on, for example, structures of pores (for example, the porosity and the pore size) of each of the porous protective layer and the detection electrode, and the presence or absence of the porous protective layer. In the case where the interaction term correlates with the combustion of ammonia, the constant γ of the interaction term can vary depending on the operating temperature of the mixed potential cell. For example, a higher operating temperature can result in a larger absolute value of the constant γ.

Formulae (A16) and (1) are not limited to the case where the target gas has a total pressure of 1 atm, and can also be applied to the case where the total pressure is about 1 atm (for example, 0.9 atm to 1.10 atm). Formulae (A16) and (1)

can also be applied to the case where the total pressure of the target gas is not about 1 atm. The temperature of the target gas to which formula (1) is applied may be, but is not particularly limited to, 150° C. or higher or 200° C. or higher. The temperature of the target gas may be 400° C. or lower.

Figure 4:
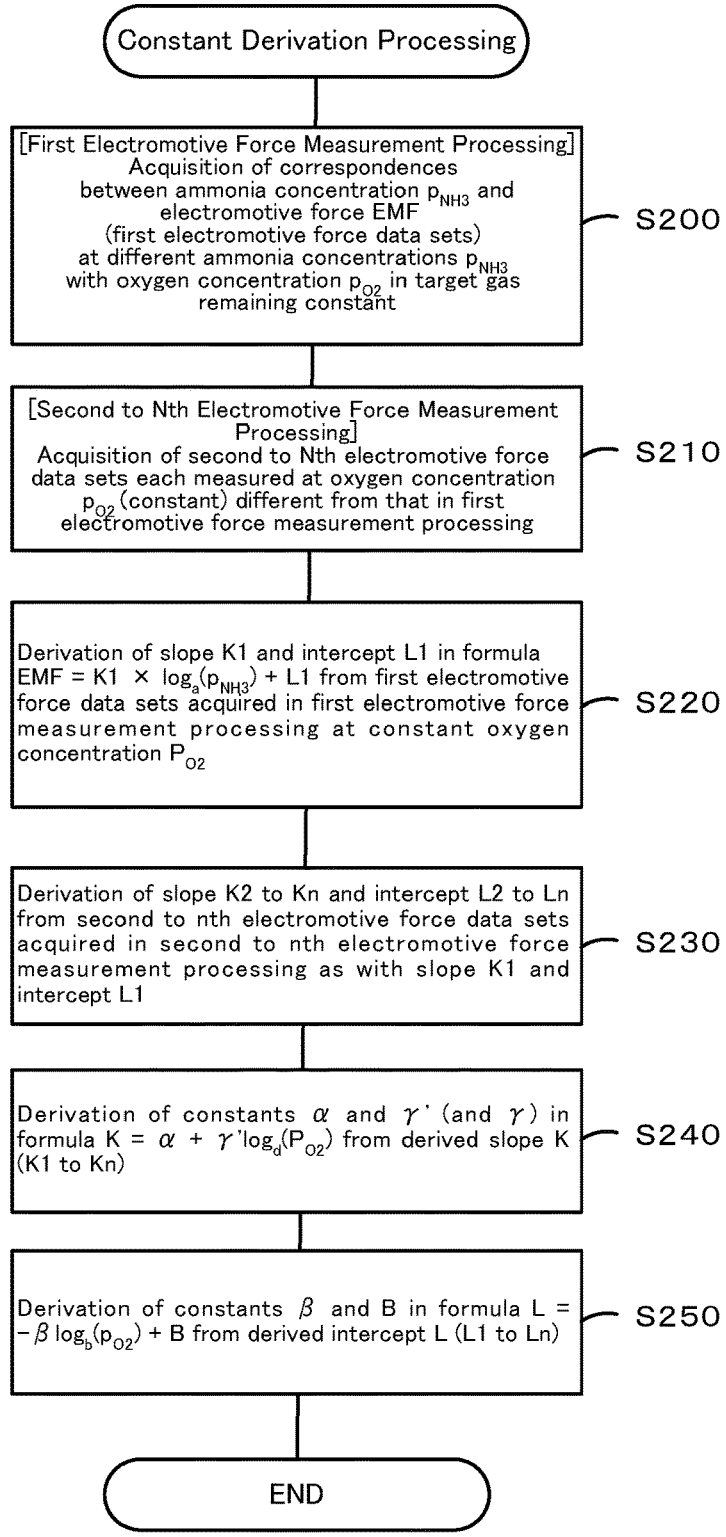
FIG. 4 is a flow chart illustrating an example of a constant derivation processing.

The constants α, β, γ, and B in formula (1) can be determined by experiments as described below, in advance. FIG. 4 is a flow chart illustrating an example of constant derivation processing. In the constant derivation processing, the sensor element 31, which is a target with the constants to be derived, is subjected to first electromotive force measurement processing for acquiring first electromotive force data multiple times, the first electromotive force data expressing the correspondence between the ammonia concentration $p_{NH3}$ and the electromotive force EMF (step S200). Specifically, the correspondence between the ammonia concentration $p_{NH3}$ and the electromotive force EMF is acquired as the first electromotive force data by exposing the sensor element 31 to the target gas with the oxygen concentration $p_{O2}$ and the ammonia concentration $p_{NH3}$ that have been adjusted to predetermined values and measuring the electromotive force EMF. Next, first electromotive force data sets are similarly acquired by measuring the electromotive force EMF multiple times at different ammonia concentrations $p_{NH3}$ in the target gas while the oxygen concentration $p_{O2}$ in the target gas remains unchanged (constant). Subsequently, as with the first electromotive force measurement processing, electromotive force EMF measurement processing that is executed multiple times at different ammonia concentrations $p_{NH3}$ while the oxygen concentration $p_{O2}$ remains unchanged (constant) is executed multiple times at different oxygen concentrations $p_{O2}$ (second to nth electromotive force measurement processing) to acquire the second to the nth electromotive force data sets (step S210). n represents an integer of 2 or more. For example, only the second electromotive force measurement processing may be executed in step S210.

Next, the slope K (here, K1) and the intercept L (here, L1) of formula (3) described below are derived from the first electromotive force data sets acquired in step S200 (step S220). In the case where formula (1a) described above is regarded as a linear function of the electromotive force EMF and the logarithm of the ammonia concentration $p_{NH3}$, i.e., $\log_a(p_{NH3})$, the slope K and the intercept L are defined by formulae (3) and (4), respectively, and formula (1a) can thus be expressed by formula (5). As is clear from formulae (3) and (4), each of the slope K and the intercept L is constant at a constant oxygen concentration $p_{O2}$; hence, on the basis of the first electromotive force data sets (data sets at a constant oxygen concentration $p_{O2}$), the slope K (K1) and the intercept L (L1) corresponding to the oxygen concentration $p_{O2}$ at the time of the measurement of the data sets can be derived. Specifically, the slope and the intercept obtained when the relationship between the logarithm of the ammonia concentration $p_{NH3}$, $\log_a(p_{NH3})$, and the electromotive force EMF in the first electromotive force data sets acquired by executing the first electromotive force measurement processing multiple times is approximated by a straight line (linear function) are derived as the slope K1 and the intercept L1. The approximation is performed on the basis of, for example, the method of least squares. Subsequently, as with step S220, the slopes K2 to Kn and the intercepts L2 to Ln are derived (step S230) in the same way as the slope K1 and the intercept L1 on the basis of the second to the nth electromotive force data sets acquired in step S210.

$$K=\alpha+\gamma' \log_d(p_{O2}) \quad (3)$$

$$L=-\beta \log_b(p_{O2})+B \quad (4)$$

$$EMF=K \times \log_a(p_{NH3})+L \quad (5)$$

Subsequently, the constants α and γ' are derived from formula (3) described above (step S240) on the basis of the correspondences between the slopes K (K1 to Kn) derived in steps S220 and S230 and the oxygen concentrations $p_{O2}$ at the time of the derivation of the slopes K1 to Kn (for example, in the cases of the slope K1, the oxygen concentration $p_{O2}$ at the time of the first electromotive force data measurement). As is clear from formula (3), the slope K is a linear function of the logarithm of the oxygen concentration $p_{O2}$, i.e., $\log_d(p_{O2})$. When the relationship between the $\log_d(p_{O2})$ and the slope K is approximated by a straight line (linear function), the slope is derived as the constant γ', and the intercept is derived as the constant α. By deriving the constant γ', the constant γ can be derived (see the proviso of formula (1a)). When base a=base c, constant γ'=constant γ.

As with the step S240, the constants β and B are derived from formula (4) on the basis of the correspondences between the intercepts L (L1 to Ln) derived in steps S220 and S230 and the oxygen concentrations $p_{O2}$ at the time of the derivation of the intercepts L1 to Ln (for example, in the cases of the intercept L1, the oxygen concentration $p_{O2}$ at the time of the first electromotive force data measurement) (step S250). As is clear from formula (4), the intercept L is a linear function of the logarithm of the oxygen concentration $p_{O2}$, i.e., $\log_b(p_{O2})$. When the relationship between the $\log_b(p_{O2})$ and the intercept L is approximated by a straight line (linear function), the slope is derived as the constant β, the intercept is derived as the constant B. Thereby, the constants α, β, γ, and B are derived, and this processing is completed.

Each of the first to the nth electromotive force data sets described above is measured in a state in which the mixed potential cell 55 is heated with the heater 62 to a predetermined fixed operating temperature. Comparisons between formula (1) and formula (A15) reveal that the constants α and β vary depending on the temperature T of the mixed potential cell 55, i.e., the operating temperature of the sensor element 31 in use. Thus, in the case where one sensor element 31 can be used at different operating temperatures, the constants α and β in formula (1) are derived at each of the different operating temperatures and stored in, for example, the memory part 73, in advance. When the control section 72 executes the ammonia concentration derivation processing, the constants α and β corresponding to the operating temperature of the sensor element 31 are used. The constant γ can vary depending on the operating temperature of the mixed potential cell 55 as described above; thus, a value corresponding to the operating temperature of the mixed potential cell 55 is derived and stored in, for example, the memory part 73, in advance. The constant B can also vary depending on the operating temperature of the sensor element 31 in use; thus, the constant B may be derived at each of the different operating temperatures and stored in, for example, the memory part 73, in advance.

A method other than the foregoing constant derivation processing may be employed as long as the constants α, β, γ, and B can be derived. For example, in step S200, the electromotive force EMF may be measured multiple times at different oxygen concentrations $p_{O2}$ in the target gas while the ammonia concentration $p_{NH3}$ is constant (the same is true for step S210). The constant derivation processing is not limited to the case where the electromotive force EMF is measured multiple times while one of the ammonia concentration $p_{NH3}$ and the oxygen concentration $p_{O2}$ is constant and the other is changed. The electromotive forces EMFs may be measured with at least four target gases in which at least one of the ammonia concentration $p_{NH3}$ and the oxygen concentration $p_{O2}$ is different when the sensor element 31 is exposed to each of the target gases. If at least four correspondences (electromotive force data sets) among the electromotive forces EMFs, the oxygen concentrations $p_{O2}$, and the ammonia concentrations $p_{NH3}$ are thus acquired, simultaneous equations are solved by replacing variables in formula (1) by the values of the electromotive force data sets, so that the constants α, β, γ, and B can be derived. Like the foregoing constant derivation processing, however, the constants are preferably derived from the electromotive force data sets as many as possible.

Let us now clarify the correspondence between the constituent elements of this embodiment and constituent elements of the present invention. The solid electrolyte layer 44 of this embodiment corresponds to a solid electrolyte body of the present invention. The detection electrode 51 corresponds to a detection electrode. The reference electrode 53 corresponds to a reference electrode. The mixed potential cell 55 corresponds to a mixed potential cell. The electromotive force acquisition section 75 corresponds to a electromotive force acquisition section. The oxygen concentration acquisition section 76 corresponds to an oxygen concentration acquisition section. The control section 72 corresponds to an ammonia concentration derivation section. In this embodiment, an example of a method for measuring ammonia concentration of the present invention is also described by explaining the operation of the apparatus 70 for measuring ammonia concentration.

According to the system 2 for treating an exhaust gas described above in detail, in the apparatus 70 for measuring ammonia concentration, the use of the relationship of formula (1) can derive the ammonia concentration in the target gas with higher accuracy than that in the case of using formula (2) described above.

The target gas may have a temperature of 150° C. or higher. The derivation of the ammonia concentration $p_{NH3}$ using the relationship of formula (1) is suitable even for a high-temperature target gas.

Because the detection electrode 51 is composed of the Au—Pt alloy as a main component, the mixed potential is easily established at the triple phase boundary of the solid electrolyte layer 44 and the target gas. The detection electrode 51 has a degree of concentration of 0.3 or more, which is measured by at least one of XPS and AES, and thus enables the mixed potential to be more reliably established.

Because the operating temperature of the mixed potential cell 55 is 450° C. or higher, the solid electrolyte layer 44 can be appropriately activated. Because the operating temperature of the mixed potential cell 55 is 650° C. or lower, a decrease in measurement accuracy due to the combustion of ammonia can be inhibited.

The system 2 for treating an exhaust gas includes the one or more oxidation catalysts (DOC 4 and ASC 8) arranged in the exhaust gas path 3, and the sensor element 31 is arranged on the downstream side of the exhaust gas path 3 in contrast to the DOC 4, which is one of the one or more oxidation catalysts, arranged at the upstream end. Thus, the target gas in which a component (for example, at least one of hydrocarbons and carbon monoxide) that is present in the target gas and that affects the measurement accuracy of the ammonia concentration has been oxidized by the oxidation catalysts reaches the sensor element 31. Accordingly, in the system 2 for treating an exhaust gas, the ammonia concentration in the target gas can be derived with higher accuracy.

The present invention is not limited to the above-described embodiment, and can be carried out by various modes as long as they belong to the technical scope of the invention.

For example, in the foregoing embodiment, although the detection electrode 51 and the reference electrode 53 are arranged on the solid electrolyte layer 44, the solid electrolyte layer 44 is not necessarily used, and they may be arranged on a solid electrolyte body. For example, the detection electrode 51 and the reference electrode 53 may be arranged on upper and lower surfaces of a solid electrolyte body including solid electrolyte layers stacked. In the foregoing embodiment, although the reference electrode 53 serves as both of the reference electrode of the mixed potential cell 55 and the reference electrode of the concentration cell 56, this structure is not necessarily used, and the mixed potential cell 55 and the concentration cell 56 may include different reference electrodes.

In the foregoing embodiment, although the sensor element 31 includes the concentration cell 56 and thus can measure the oxygen concentration, this structure is not necessarily used. The sensor element 31 may not include the concentration cell 56 (specifically, the auxiliary electrode 52). In this case, the apparatus 70 for measuring ammonia concentration may acquire information about the oxygen concentration from other than the sensor element 31. For example, the apparatus 70 for measuring ammonia concentration may acquire information about the oxygen concentration from another sensor that is arranged in the exhaust gas path 3 and that can detect information about the oxygen concentration (for example, an oxygen sensor, an A/F sensor, or a NOx sensor). The apparatus 70 for measuring ammonia concentration may acquire information about the oxygen concentration from another device (such as the engine ECU 9) other than sensors. In the case where the apparatus 70 for measuring ammonia concentration acquires information about the oxygen concentration from another sensor arranged at a position of the exhaust gas path 3, the position being different from that of the sensor element 31, the apparatus 70 for measuring ammonia concentration preferably derives the ammonia concentration in consideration of a measurement time lag (time lag C) the difference in position between the sensor element 31 and due to the another sensor attached. Specifically, letting the length of time that the target gas flow from the position of one, located upstream, of the sensor element 31 and the another sensor to the position of the other in the exhaust gas path 3 be the time lag C, the apparatus 70 for measuring ammonia concentration preferably derives the ammonia concentration in consideration of the time lag C. For example, in the case where the another sensor is located on the upstream side of the sensor element 31, the control section 72 allows the memory part 73 to store the values of oxygen concentration acquired from the another sensor every predetermined period during the time lag C. Every time the electromotive force EMF is acquired from the sensor element 31, the control section 72 reads the oldest value of oxygen concentration at that time (=value acquired in the past by the time lag C) from the memory part 73 and derives the ammonia concentration from the acquired electromotive force EMF, the value of the oxygen concentration read, and formula (1). In this way, the apparatus 70 for measuring ammonia concentration can derive the ammonia concentration with higher accuracy by considering the time lag C.

Although the engine 1 is a diesel engine in the foregoing embodiment, a gasoline engine may be used.

In the foregoing embodiment, although the apparatus 70 for measuring ammonia concentration is an apparatus different from the engine ECU 9, the apparatus 70 for measuring ammonia concentration may be part of the engine ECU 9.

EXAMPLES

Examples in which a method for measuring ammonia concentration was specifically performed will be described below as Examples. The present invention is not limited to Examples described below.

Production of Sensor Element 1

A sensor element to be used for the measurement of ammonia concentration with an apparatus for measuring ammonia concentration was produced. Four ceramic green sheets containing a ceramic component composed of a zirconia solid electrolyte containing 3% by mole yttria serving as a stabilizer were prepared as the layers of the base 40. For example, sheet holes used for positioning during printing and stacking and through-holes required were formed in the green sheets. A space to be formed into the reference gas introduction cavity 46 was formed in the green sheet to be formed into the spacer layer 43 by, for example, punching, in advance. Various patterns were formed by pattern printing on the ceramic green sheets corresponding to the first substrate layer 41, the second substrate layer 42, the spacer layer 43, and the solid electrolyte layer 44, and the resulting ceramic green sheets were subjected to drying treatment. Specifically, for example, patterns for the detection electrode 51 composed of the Au—Pt alloy, the auxiliary electrode 52 and the reference electrode 53 composed of Pt, lead wires, and the heater portion 60 were formed. The pattern printing was performed by applying pattern-forming pastes to the green sheets using a known screen printing technique, each of the pattern-forming pastes being prepared to provide characteristics required for a corresponding one of the target objects. After the pattern printing and the drying were completed, printing and drying treatment of a bonding paste to stack and bond the green sheets corresponding to the layers together were performed. Compression bonding treatment was performed in which the green sheets including the bonding paste were stacked in a predetermined order while the green sheets were positioned with the sheet holes, and the resulting stack were subjected to compression bonding under predetermined temperature and pressure conditions to form a laminate. Laminated pieces having the same size as the sensor element 31 were cut from the resulting laminate. The cut laminated pieces were fired with a tubular furnace at 1,100° C. for 2 hours in an air atmosphere, thereby providing the sensor elements 31 each including the detection electrode 51, the auxiliary electrode 52, and the reference electrode 53 that were arranged on the solid electrolyte layer 44. The sensor elements 31 were subjected to dipping with an alumina-containing slurry and firing to form the porous protective layers 48 on surfaces of the sensor elements 31. In this way, the sensor element 31 was produced and was referred to as a sensor element 1. The degree of concentration on the surface of a noble metal on the fracture surface of the detection electrode 51 in the sensor element 1 was measured by AES and found to be 0.99. The detection electrode 51 had a porosity of 45% by volume. The porous protective layer 48 had a porosity of 40% by volume. In the following tests, the operating temperature of the sensor element 1 in use was 480° C.

Experiment 1: Acquisition of Electromotive Force Data Sets

Figure 5:
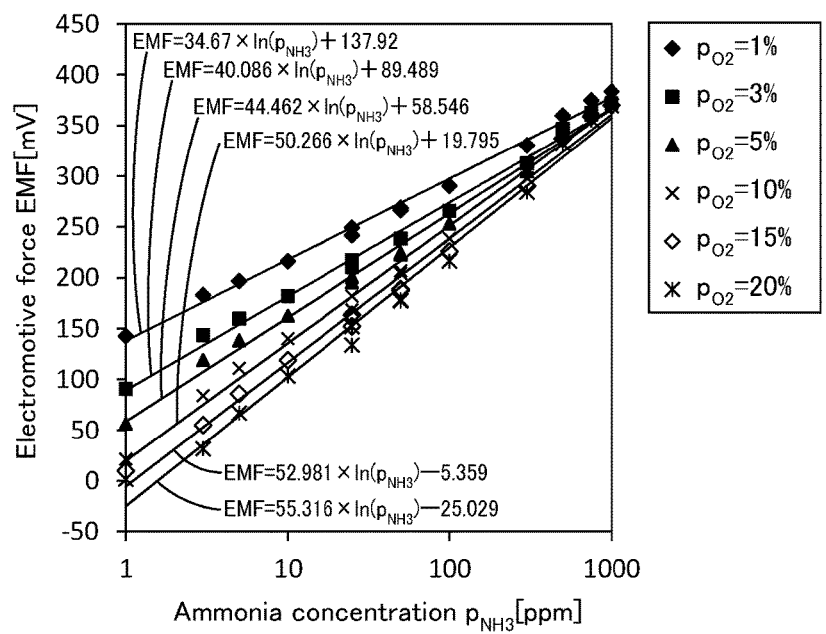
FIG. 5 is a graph depicting the relationships between ammonia concentrations $p_{NH3}$ [ppm] and electromotive forces EMFs [mV] of a sensor element 1.

The sensor element 1 was subjected to steps S200 and S210 in the constant derivation processing to acquire first to sixth electromotive force data sets (13 for each data set). The first electromotive force data was acquired by measuring the electromotive forces EMFs [mV] at a fixed oxygen concentration $p_{O2}$ of 1%, a fixed $H_2O$ concentration $p_{H2O}$ of 5%, and different ammonia concentrations $p_{NH3}$, as listed in Table 1, in a target gas. A component (base gas) other than the foregoing components in the target gas was nitrogen, and the temperature was 200° C. The target gas was allowed to flow through the pipe having a diameter of 70 mm at a flow rate of 200 L/min. The second to the sixth electromotive force data sets were measured as in the first electromotive force data, except that the oxygen concentration $p_{O2}$ (fixed value) in the target gas was changed as listed in Table 1. Table 1 lists the ammonia concentrations $p_{NH3}$, the oxygen concentrations $p_{O2}$, and the electromotive forces EMFs of the first to the sixth electromotive force data sets measured. FIG. 5 is a graph depicting the relationship between the ammonia concentration $p_{NH3}$ [ppm] and the electromotive force EMF [mV] of the sensor element 1 (first to sixth electromotive force data sets). The horizontal axis of FIG. 5 is on a logarithmic scale. FIG. 5 indicates that the relationships between the logarithms of the ammonia concentrations $p_{NH3}$ at fixed oxygen concentrations $p_{O2}$ and the electromotive forces EMFs can be approximated by a straight line. The results indicated that higher oxygen concentrations $p_{O2}$ resulted in higher slopes K of the straight lines and that higher oxygen concentrations $p_{O2}$ resulted in lower intercepts L of the straight lines. The results also indicated that the ratio of the $NH_3$ sensitivity to the $O_2$ interference in the measured values of the electromotive force EMF was not always (⅔):(½). These results indicated that the relationship among the electromotive force EMF, the ammonia concentration $p_{NH3}$, and the oxygen concentration $p_{O2}$ was not matched to formula (2).

TABLE 1

| $p_{NH3}$[ppm] | First electromotive force data $p_{O2}$ = 1% EMF[mV] | Second electromotive force data $p_{O2}$ = 3% EMF[mV] | Third electromotive force data $p_{O2}$ = 5% EMF[mV] | Fourth electromotive force data $p_{O2}$ = 10% EMF[mV] | Fifth electromotive force data $p_{O2}$ = 15% EMF[mV] | Sixth electromotive force data $p_{O2}$ = 20% EMF[mV] |
|---|---|---|---|---|---|---|
| 25 | 241.850 | 210.583 | 195.600 | 168.633 | 152.050 | 133.750 |
| 50 | 266.217 | 238.567 | 224.333 | 204.550 | 187.783 | 177.417 |
| 100 | 290.133 | 265.967 | 262.200 | 238.650 | 225.700 | 216.350 |
| 300 | 330.183 | 312.467 | 304.617 | 298.050 | 290.250 | 284.333 |

TABLE 1-continued

| $p_{NH3}$[ppm] | First electromotive force data $p_{O2}$ = 1% EMF[mV] | Second electromotive force data $p_{O2}$ = 3% EMF[mV] | Third electromotive force data $p_{O2}$ = 5% EMF[mV] | Fourth electromotive force data $p_{O2}$ = 10% EMF[mV] | Fifth electromotive force data $p_{O2}$ = 15% EMF[mV] | Sixth electromotive force data $p_{O2}$ = 20% EMF[mV] |
|---|---|---|---|---|---|---|
| 500 | 359.783 | 346.433 | 341.917 | 341.667 | 336.800 | 332.200 |
| 750 | 374.767 | 362.800 | 360.567 | 362.733 | 358.917 | 355.583 |
| 1000 | 373.600 | 371.967 | 373.867 | 376.900 | 369.883 | 369.600 |
| 1 | 142.917 | 90.817 | 56.233 | 21.467 | 9.833 | 1.667 |
| 3 | 182.983 | 143.367 | 119.083 | 84.017 | 55.233 | 31.650 |
| 5 | 196.833 | 159.933 | 138.467 | 111.200 | 85.883 | 66.933 |
| 10 | 216.133 | 182.033 | 162.683 | 140.300 | 118.900 | 103.367 |
| 25 | 249.083 | 217.117 | 200.700 | 182.100 | 163.600 | 151.983 |
| 50 | 268.500 | 238.500 | 222.883 | 206.400 | 188.733 | 178.200 |

Experiment 2: Derivation of Slope K and Intercept L

Figure 6:
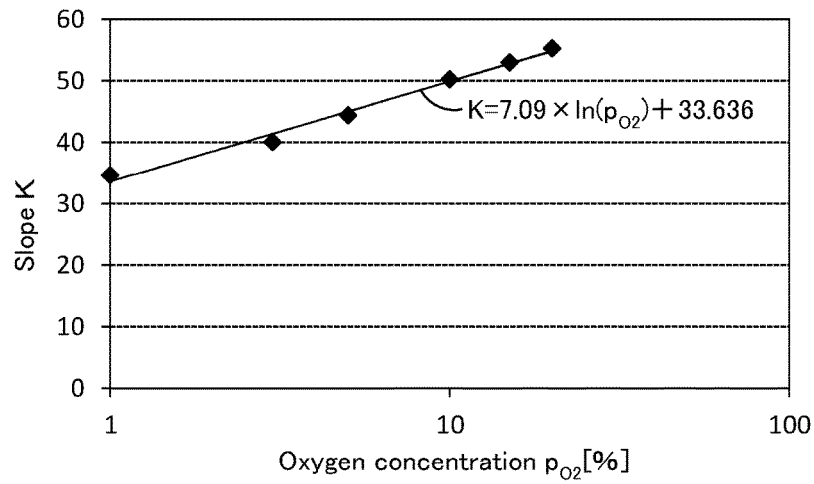
FIG. 6 is a graph depicting the relationship between the oxygen concentration $p_{O2}$ and the slope K of the sensor element 1.
Figure 7:
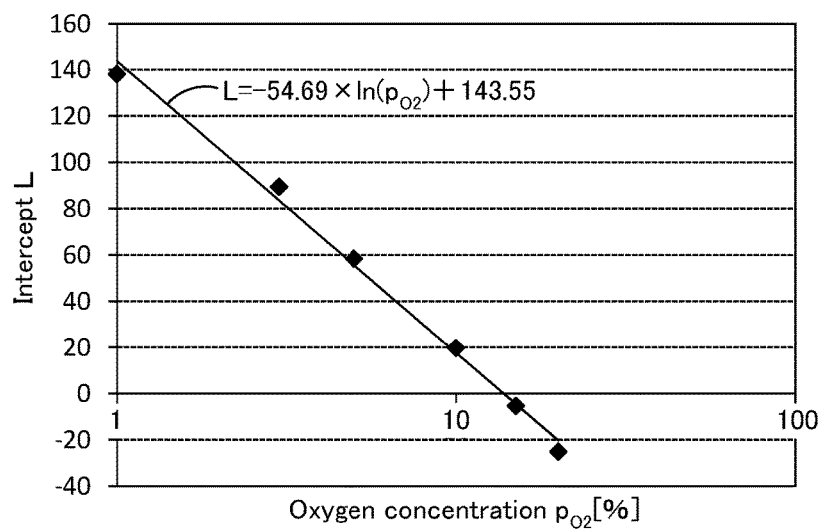
FIG. 7 is a graph depicting the relationship between the oxygen concentration $p_{O2}$ and the intercept L of the sensor element 1.

Subsequently, steps S220 and S230 in the constant derivation processing were executed to derive the slopes K (K1 to K6) and the intercepts L (L1 to L6) in the first to the sixth electromotive force data sets. For example, with regard to the approximate straight line at an oxygen concentration $p_{O2}$ of 1% (first electromotive force data) illustrated in FIG. 5, the slope was defined as K1 (=34.67), and the intercept was defined as L1 (=137.92). The intercept L1 is a value of the electromotive force EMF when $\log_a(p_{NH3})$ of the approximate straight line is zero, in other words, when $p_{NH3}$ is 1 ppm. Table 2 lists the derived slopes K, the derived intercepts L, and the oxygen concentrations $p_{O2}$ corresponding thereto. FIG. 6 is a graph depicting the relationship between the oxygen concentration $p_{O2}$ and the slope K listed in Table 2. FIG. 7 is a graph depicting the relationship between the oxygen concentration $p_{O2}$ and the intercept L listed in Table 2. The horizontal axis of each of FIGS. 6 and 7 is on a logarithmic scale. FIG. 6 indicates that the relationship between the logarithm of the oxygen concentration $p_{O2}$ and the slope K can be approximated by a straight line. FIG. 7 indicates that the relationship between the logarithm of the oxygen concentration $p_{O2}$ and the intercept L can be approximated by a straight line.

TABLE 2

| | $p_{O2}$[%] | Slope K | Intercept L |
|---|---|---|---|
| First electromotive force data | 1 | 34.670 | 137.920 |
| Second electromotive force data | 3 | 40.086 | 89.489 |
| Third electromotive force data | 5 | 44.462 | 58.546 |
| Forth electromotive force data | 10 | 50.266 | 19.795 |
| Fifth electromotive force data | 15 | 52.981 | −5.359 |
| Sixth electromotive force data | 20 | 55.316 | −25.029 |

Experiment 3: Derivation of Constants α, β, γ, and B

Steps S240 and S250 in the constant derivation processing were executed on the basis of the data sets obtained in experiments 1 and 2 to derive the constants α, β, γ, and B of the sensor element 1. Specifically, formula (6) described below was derived as an approximate straight line expressing the relationship between the logarithm of the oxygen concentration $p_{O2}$ and the slope K illustrated in FIG. 6. The constant γ'=7.09 and the constant α=33.636 were derived from formula (6). Formula (7) described below was derived as an approximate straight line expressing the relationship between the logarithm of the oxygen concentration $p_{O2}$ and the intercept L illustrated in FIG. 7. The constant β=54.69 and the constant B=143.55 were derived from formula (7). In a formula derived here, each of the bases a to d in formula (1) was Napier's constant e. Thus, γ=γ'=7.09 was derived.

$$K = 7.09 \times \ln(p_{O2}) + 33.636 \quad (6)$$

$$L = -54.69 \times \ln(p_{O2}) + 143.55 \quad (7)$$

From experiments 1 to 3 described above, formula (8) expressing the relationship among the variables (EMF, $p_{NH3}$, and $p_{O2}$) in the sensor element 1 was derived. In formula (8), the units of the electromotive force EMF are [mV], the units of the ammonia concentration $p_{NH3}$ are [ppm], and the units of the oxygen concentration $p_{O2}$ are [%].

$$EMF = 33.636 \times \ln(p_{NH3}) - 54.69 \times \ln(p_{O2}) + 7.09 \times \ln(p_{NH3}) \times \ln(p_{O2}) + 143.55 \quad (8)$$

Verification Test

Figure 8:
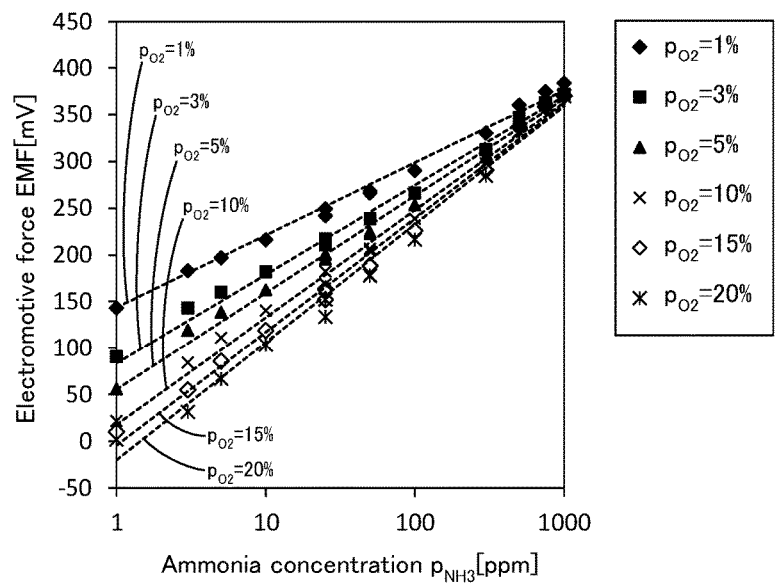
FIG. 8 is a graph depicting actually measured electromotive forces EMFs of the sensor element 1 and straight lines derived from formula (8).

The electromotive forces EMFs corresponding to ammonia concentrations $p_{NH3}$ and oxygen concentrations $p_{O2}$ were derived from formula (8) under the same conditions as those in the first to the sixth electromotive force data sets. Table 3 lists the results. FIG. 8 is a graph illustrating six straight lines represented by a formula (formula corresponding to formula (5)) derived from formula (8) at the different oxygen concentrations $p_{O2}$ used in the first to the sixth electromotive force data sets. FIG. 8 also illustrates the points of the first to the sixth electromotive force data sets (measured values) illustrated in FIG. 5. FIG. 8 and comparisons between Tables 1 and 3 indicated that the measured values of the electromotive forces EMFs were matched to the electromotive forces EMFs derived from formula (8) with good accuracy. That is, although the relationship among the electromotive force EMF, the ammonia concentration $p_{NH3}$, and the oxygen concentration $p_{O2}$ based on actual measurement was not expressed by formula (2) as illustrated in FIG. 5, the relationship based on the measured values was able to be expressed by formula (8) derived from formula (1). These results indicated that the use of formula (1) was able to derive the ammonia concentration $p_{NH3}$ with higher accuracy than that in the case of using formula (2).

TABLE 3

| $p_{NH3}$[ppm] | $p_{O2}$ = 1% EMF[mV] | $p_{O2}$ = 3% EMF[mV] | $p_{O2}$ = 5% EMF[mV] | $p_{O2}$ = 10% EMF[mV] | $p_{O2}$ = 15% EMF[mV] | $p_{O2}$ = 20% EMF[mV] |
|---|---|---|---|---|---|---|
| 1 | 143.550 | 83.467 | 55.530 | 17.622 | −4.553 | −20.287 |
| 3 | 180.503 | 128.977 | 105.019 | 72.510 | 53.493 | 40.001 |
| 5 | 197.685 | 150.138 | 128.030 | 98.031 | 80.483 | 68.033 |
| 10 | 221.000 | 178.852 | 159.254 | 132.662 | 117.106 | 106.069 |
| 25 | 251.820 | 216.809 | 200.530 | 178.441 | 165.520 | 156.352 |
| 50 | 275.135 | 245.523 | 231.754 | 213.071 | 202.143 | 194.389 |
| 100 | 298.450 | 274.237 | 262.979 | 247.702 | 238.766 | 232.426 |
| 300 | 335.402 | 319.747 | 312.468 | 302.590 | 296.812 | 292.713 |
| 500 | 352.585 | 340.908 | 335.479 | 328.112 | 323.802 | 320.745 |
| 750 | 366.223 | 357.704 | 353.744 | 348.369 | 345.225 | 342.995 |
| 1000 | 375.899 | 369.622 | 366.703 | 362.742 | 360.425 | 358.782 |

Figure 9:
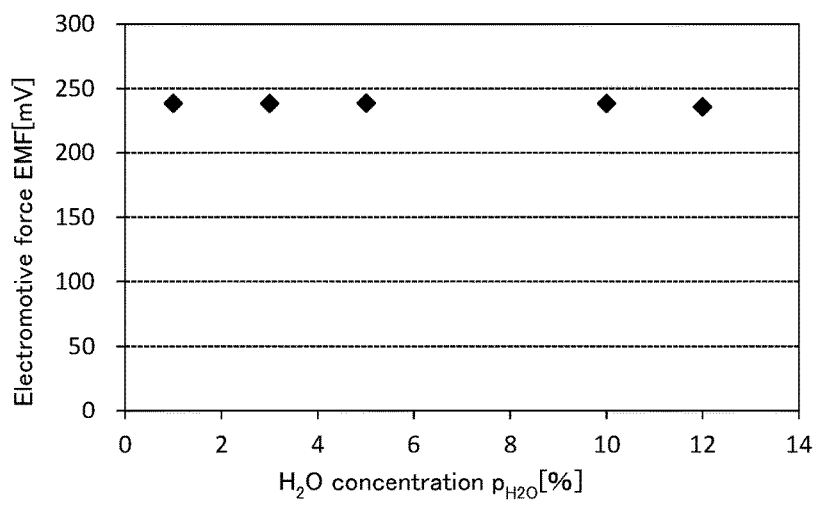
FIG. 9 is a graph depicting the relationship between the $H_2O$ concentration $p_{H2O}$ [%] and the electromotive force EMF [mV] of the sensor element 1.

The electromotive forces EMFs of the sensor element 1 were measured with target gases having a constant ammonia concentration $p_{NH3}$ of 100 ppm, a constant oxygen concentration $p_{O2}$ of 10%, and different $H_2O$ concentrations $p_{H2O}$ of 1% to 12% as listed in Table 4. Conditions other than those described above were the same as in experiment 1. FIG. 9 is a graph depicting the relationship between the $H_2O$ concentration $p_{H2O}$ [%] and the electromotive force EMF [mV] of the sensor element 1. FIG. 9 indicated that the electromotive force EMF remains almost unchanged at different $H_2O$ concentrations $p_{H2O}$ in the target gases (substantially no $H_2O$ interference). That is, the results indicated that the term of the $H_2O$ concentration $p_{H2O}$ in formula (2) was not matched to the relationship between the electromotive force EMF and the $H_2O$ concentration $p_{H2O}$ actually measured.

TABLE 4

| $p_{H2O}$[%] | EMF[mV] |
|---|---|
| 1 | 238.65 |
| 3 | 238.65 |
| 5 | 238.65 |
| 10 | 238.65 |
| 12 | 235.65 |

The present application claims priority from U.S. provisional Patent Application No. 62/411,736 filed on Oct. 24, 2016 and Japanese Patent Application No. 2017-117089 filed on Jun. 14, 2017, the entire contents of which are incorporated herein by reference.

What is claimed is:

1. An apparatus for measuring ammonia concentration in a target gas with a sensor element including a mixed potential cell that includes a solid electrolyte body, a detection electrode arranged on the solid electrolyte body, and a reference electrode arranged on the solid electrolyte body, the apparatus comprising:
   a first detection circuit connected to the detection electrode and the reference electrode, the detection electrode having a detection sensitivity to ammonia concentration in the target gas and establishing a mixed potential depending on the ammonia concentration in the target gas, the first detection circuit measuring an electromotive force (EMF) between the detection electrode and the reference electrode;
   a second detection circuit that measures oxygen concentration in the target gas;
   a processor coupled to the first and second detection circuits and to a memory, the memory storing instructions that when executed configure the processor to:
   acquire information from the first detection circuit about the electromotive force of the mixed potential cell while the detection electrode is exposed to the target gas;
   acquire information from the second detection circuit about oxygen concentration in the target gas;
   derive the ammonia concentration in the target gas based on the acquired information about the electromotive force, the acquired information about the oxygen concentration, and a relationship represented by formula (1):

$$EMF = \alpha \log_a(p_{NH3}) - \beta \log_b(p_{O2}) + \gamma \log_c(p_{NH3}) \times \log_d(p_{O2}) + B \quad (1)$$

(where
   EMF: an electromotive force of the mixed potential cell,
   α, β, γ, and B: constants (provided that each of α, β, and γ≠0),
   a, b, c, and d: any base (provided that each of a, b, c, and d≠1, and each of a, b, c, and d>0),
   $p_{NH3}$: the ammonia concentration in the target gas, and
   $p_{O2}$: the oxygen concentration in the target gas); and
   store the derived ammonia concentration in the target gas in the memory.

2. A system for measuring ammonia concentration, comprising:
   the apparatus for measuring ammonia concentration according to claim 1; and
   the sensor element.

3. The system for measuring ammonia concentration according to claim 2,
   wherein the detection electrode is composed of a Au—Pt alloy as a main component.

4. The system for measuring ammonia concentration according to claim 3,
   wherein the detection electrode has a degree of concentration (=amount of Au present [atom %]/amount of Pt present [atom %]) of 0.3 or more, the degree of concentration being measured by at least one of X-ray photoelectron spectroscopy (XPS) and Auger electron spectroscopy (AES).

5. The system for measuring ammonia concentration according to claim 2,
   wherein the sensor element includes a heater configured to heat the mixed potential cell to an operating temperature of 450° C. or higher and 650° C. or lower.

6. A system for treating an exhaust gas, comprising:
   the system for measuring ammonia concentration according to claim 2; and
   an exhaust gas path through which an exhaust gas serving as the target gas from an internal combustion engine flows, the sensor element being arranged in the exhaust gas path.

7. The system for treating an exhaust gas according to claim 6, further comprising:
one or more oxidation catalysts arranged in the exhaust gas path,
wherein the sensor element is arranged on the downstream side of the exhaust gas path in contrast to one of the one or more oxidation catalysts arranged at an upstream end.

8. A method for measuring ammonia concentration in a target gas with a sensor element including a mixed potential cell that includes a solid electrolyte body, a detection electrode arranged on the solid electrolyte body, and a reference electrode arranged on the solid electrolyte body, the method comprising:
measuring, with a first detection circuit connected to the detection electrode and the reference electrode, an electromotive force (EMF) between the detection electrode and the reference electrode, the detection electrode having a detection sensitivity to ammonia concentration in the target gas and establishing a mixed potential depending on the ammonia concentration in the target gas;
measuring with a second detection circuit an oxygen concentration in the target gas;
acquiring information, via a processor, from the first detection circuit about the electromotive force of the mixed potential cell while the detection electrode is exposed to the target gas;
acquiring information, via the processor, from the second detection circuit about oxygen concentration in the target gas;
deriving, via the processor, the ammonia concentration in the target gas based on the acquired information about the electromotive force, the acquired information about the oxygen concentration, and a relationship represented by formula (1):

$$\text{EMF} = \alpha \log_a(p_{NH3}) - \beta \log_b(p_{O2}) + \gamma \log_c(p_{NH3}) \times \log_d(p_{O2}) + B \quad (1)$$

(where
EMF: an electromotive force of the mixed potential cell,
$\alpha$, $\beta$, $\gamma$, and B: constants (provided that each of $\alpha$, $\beta$, and $\gamma \neq 0$),
a, b, c, and d: any base (provided that each of a, b, c, and $d \neq 1$, and each of a, b, c, and $d > 0$),
$p_{NH3}$: the ammonia concentration in the target gas, and
$p_{O2}$: the oxygen concentration in the target gas); and
generating an electrical signal, via the processor, depending on the derived ammonia concentration in the target gas.

9. The method for measuring ammonia concentration according to claim 8, further including the target gas being an exhaust gas passing through an exhaust pipe of an internal combustion engine, wherein the sensor element is arranged in a path of the exhaust gas and the measured ammonia concentration is used by a controller for controlling an amount of at least one of ammonia and a substance capable of forming ammonia that is to be injected into the exhaust pipe.

* * * * *